(12) United States Patent
Stone et al.

(10) Patent No.: US 8,109,965 B2
(45) Date of Patent: Feb. 7, 2012

(54) METHOD AND APPARATUS FOR SOFT TISSUE FIXATION

(75) Inventors: Kevin T Stone, Winona Lake, IN (US); Ryan A Kaiser, Leesburg, IN (US); Nathan Sautter, North Manchester, IN (US)

(73) Assignee: Biomet Sports Medicine, LLP, Warsaw, IN (US)

( * ) Notice: Subject to any disclaimer, the term of this patent is extended or adjusted under 35 U.S.C. 154(b) by 1179 days.

(21) Appl. No.: 11/541,504

(22) Filed: Sep. 29, 2006

(65) Prior Publication Data

US 2007/0049944 A1 Mar. 1, 2007

Related U.S. Application Data

(63) Continuation-in-part of application No. 11/203,481, filed on Aug. 12, 2005, now Pat. No. 7,819,898, which is a continuation-in-part of application No. 10/864,900, filed on Jun. 9, 2004, now Pat. No. 7,500,983.

(51) Int. Cl.
*A61B 17/03* (2006.01)
(52) U.S. Cl. ........................................................ 606/232
(58) Field of Classification Search .................. 606/151, 606/219, 232
See application file for complete search history.

(56) References Cited

U.S. PATENT DOCUMENTS

| | | |
|---|---|---|
| 64,499 A | 6/1867 | Miller |
| 65,499 A | 6/1867 | Miller |
| 401,659 A | 4/1889 | Remington |
| 828,203 A | 12/1906 | Neil |
| 939,921 A | 11/1909 | Moeller |
| 1,077,006 A | 10/1913 | Smith |
| 1,340,470 A | 5/1920 | Whitmore |
| 1,386,202 A | 8/1921 | Peterson |
| 1,572,289 A | 2/1926 | Hogan |
| 2,061,385 A | 11/1936 | Nadler |
| 2,065,659 A | 12/1936 | Cullen |
| 2,121,193 A | 6/1938 | Hanicke |
| 2,242,003 A | 5/1941 | Lorenzo |
| 2,267,925 A | 12/1941 | Johnston |
| 2,329,398 A | 9/1943 | Duffy |
| 2,562,419 A | 7/1951 | Ferris |
| 2,600,395 A | 1/1952 | Domoj et al. |
| 2,665,597 A | 1/1954 | Hill |
| 2,698,986 A | 1/1955 | Brown |
| 2,883,096 A | 4/1959 | Dawson |
| 3,003,155 A | 10/1961 | Mielzynski et al. |
| 3,093,220 A | 6/1963 | Modrey |

(Continued)

FOREIGN PATENT DOCUMENTS

DE   2529669   3/1976

(Continued)

OTHER PUBLICATIONS

"EZ Loc Femoral Fixation Device," copyright 2005 Arthrotek, Inc. 8 sheets.

(Continued)

*Primary Examiner* — Ryan Severson
(74) *Attorney, Agent, or Firm* — Harness, Dickey

(57) ABSTRACT

A positioning member may be released to move an anchor member to a holding position. The positioning member being operable to be held in a selected orientation until the anchor member is in a selected position.

22 Claims, 15 Drawing Sheets

U.S. PATENT DOCUMENTS

| | | |
|---|---|---|
| 3,123,077 A | 3/1964 | Alcamo |
| 3,168,850 A | 2/1965 | Tennican |
| 3,399,432 A | 9/1968 | Merser |
| 3,425,475 A | 2/1969 | Bisk |
| 3,435,475 A | 4/1969 | Bisk |
| 3,470,834 A | 10/1969 | Bone |
| 3,500,820 A | 3/1970 | Almen |
| 3,513,484 A | 5/1970 | Hausner |
| 3,527,223 A | 9/1970 | Shein |
| 3,541,591 A | 11/1970 | Hoegerman |
| 3,664,345 A | 5/1972 | Dabbs et al. |
| 3,665,560 A | 5/1972 | Bennett et al. |
| 3,683,422 A | 8/1972 | Stemmer et al. |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,845,772 A * | 11/1974 | Smith ............................ 606/232 |
| 3,871,368 A | 3/1975 | Johnson et al. |
| 3,875,648 A | 4/1975 | Bone |
| 3,896,500 A | 7/1975 | Rambert et al. |
| 3,910,281 A | 10/1975 | Kletschka et al. |
| 3,931,667 A | 1/1976 | Merser et al. |
| 3,943,932 A | 3/1976 | Woo |
| 3,953,896 A | 5/1976 | Treace |
| 3,976,079 A | 8/1976 | Samuels et al. |
| 3,990,619 A | 11/1976 | Russell |
| 4,006,747 A | 2/1977 | Kronenthal et al. |
| 4,013,071 A | 3/1977 | Rosenberg |
| 4,085,466 A | 4/1978 | Goodfellow et al. |
| 4,149,277 A | 4/1979 | Bokros |
| 4,185,636 A | 1/1980 | Gabbay et al. |
| 4,210,148 A | 7/1980 | Stivala |
| 4,235,238 A | 11/1980 | Ogiu et al. |
| 4,243,037 A | 1/1981 | Smith |
| 4,273,117 A | 6/1981 | Neuhauser |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,326,531 A | 4/1982 | Shimonaka |
| 4,388,921 A | 6/1983 | Sutter et al. |
| 4,400,833 A | 8/1983 | Kurland |
| 4,409,974 A | 10/1983 | Freedland |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,493,323 A | 1/1985 | Albright et al. |
| 4,496,468 A | 1/1985 | House et al. |
| 4,532,926 A | 8/1985 | O'Holla |
| 4,537,185 A | 8/1985 | Stednitz |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,602,635 A | 7/1986 | Mulhollan et al. |
| 4,605,414 A | 8/1986 | Czajka |
| 4,621,640 A | 11/1986 | Mulhollan et al. |
| 4,632,100 A | 12/1986 | Somers et al. |
| 4,649,952 A | 3/1987 | Jobe |
| 4,653,486 A | 3/1987 | Coker |
| 4,655,777 A | 4/1987 | Dunn et al. |
| 4,667,675 A | 5/1987 | Davis |
| 4,669,473 A | 6/1987 | Richards et al. |
| 4,688,561 A | 8/1987 | Reese |
| 4,690,169 A | 9/1987 | Jobe |
| 4,708,132 A | 11/1987 | Silvestrini |
| 4,719,671 A | 1/1988 | Ito et al. |
| 4,728,332 A | 3/1988 | Albrektsson |
| 4,738,255 A | 4/1988 | Goble et al. |
| 4,741,330 A | 5/1988 | Hayhurst |
| 4,744,353 A | 5/1988 | McFarland |
| 4,744,793 A | 5/1988 | Parr et al. |
| 4,750,492 A | 6/1988 | Jacobs |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,823,794 A | 4/1989 | Pierce |
| 4,828,562 A | 5/1989 | Kenna |
| 4,851,005 A | 7/1989 | Hunt et al. |
| 4,863,383 A | 9/1989 | Grafelmann |
| 4,870,957 A | 10/1989 | Goble et al. |
| 4,893,619 A | 1/1990 | Dale et al. |
| 4,895,148 A | 1/1990 | Bays et al. |
| 4,896,668 A | 1/1990 | Popoff et al. |
| 4,898,156 A | 2/1990 | Gatturna et al. |
| 4,927,421 A | 5/1990 | Goble et al. |
| 4,946,468 A | 8/1990 | Li |
| 4,950,270 A | 8/1990 | Bowman et al. |
| 4,961,741 A | 10/1990 | Hayhurst |
| 4,968,315 A | 11/1990 | Gatturna |
| 4,979,956 A | 12/1990 | Silvestrini |
| 4,988,351 A | 1/1991 | Paulos et al. |
| 4,997,433 A | 3/1991 | Goble et al. |
| 5,002,550 A | 3/1991 | Li |
| 5,037,422 A | 8/1991 | Hayhurst et al. |
| 5,046,513 A | 9/1991 | Gatturna et al. |
| 5,062,344 A | 11/1991 | Gerker |
| 5,062,843 A | 11/1991 | Mahony |
| 5,078,731 A | 1/1992 | Hayhurst |
| 5,078,843 A | 1/1992 | Pratt |
| 5,084,050 A | 1/1992 | Draenert |
| 5,092,866 A | 3/1992 | Breard et al. |
| 5,098,433 A | 3/1992 | Freedland |
| 5,100,415 A | 3/1992 | Hayhurst |
| 5,100,417 A | 3/1992 | Cerier et al. |
| 5,116,337 A | 5/1992 | Johnson |
| 5,116,373 A | 5/1992 | Jakob et al. |
| 5,116,375 A | 5/1992 | Hofmann |
| 5,127,785 A | 7/1992 | Faucher et al. |
| 5,129,902 A | 7/1992 | Goble et al. |
| 5,129,906 A | 7/1992 | Ross et al. |
| 5,139,520 A | 8/1992 | Rosenberg |
| 5,147,362 A | 9/1992 | Goble |
| 5,152,790 A | 10/1992 | Rosenberg et al. |
| 5,156,616 A | 10/1992 | Meadows et al. |
| D331,626 S | 12/1992 | Hayhurst et al. |
| 5,176,682 A | 1/1993 | Chow |
| 5,197,987 A | 3/1993 | Koch et al. |
| 5,203,787 A | 4/1993 | Noblitt et al. |
| 5,207,679 A | 5/1993 | Li |
| 5,209,753 A | 5/1993 | Biedermann et al. |
| 5,211,647 A | 5/1993 | Schmieding |
| 5,224,946 A | 7/1993 | Hayhurst et al. |
| 5,234,435 A | 8/1993 | Seagrave, Jr. |
| 5,235,461 A | 8/1993 | Kirsch et al. |
| 5,236,445 A | 8/1993 | Hayhurst et al. |
| 5,236,461 A | 8/1993 | Forte |
| 5,246,441 A | 9/1993 | Ross |
| 5,258,016 A | 11/1993 | DiPoto et al. |
| 5,258,040 A | 11/1993 | Bruchman et al. |
| 5,268,001 A | 12/1993 | Nicholson et al. |
| 5,269,783 A | 12/1993 | Sander |
| 5,269,809 A | 12/1993 | Hayhurst et al. |
| 5,281,422 A | 1/1994 | Badylak et al. |
| 5,282,809 A | 2/1994 | Zammerer et al. |
| 5,282,832 A | 2/1994 | Toso et al. |
| 5,285,040 A | 2/1994 | Brandberg et al. |
| 5,290,217 A | 3/1994 | Campos |
| 5,306,301 A | 4/1994 | Graf et al. |
| 5,320,115 A | 6/1994 | Kenna |
| 5,320,626 A | 6/1994 | Schmieding |
| 5,324,308 A | 6/1994 | Pierce |
| 5,336,240 A | 8/1994 | Metzler et al. |
| 5,356,413 A | 10/1994 | Martins et al. |
| 5,362,294 A | 11/1994 | Seitzinger |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,379,492 A | 1/1995 | Glesser |
| 5,383,878 A | 1/1995 | Roger et al. |
| 5,391,171 A | 2/1995 | Schmieding |
| 5,393,302 A | 2/1995 | Clark et al. |

| | | |
|---|---|---|
| RE34,871 E | 3/1995 | McGuire et al. |
| 5,417,691 A | 5/1995 | Hayhurst |
| 5,417,712 A | 5/1995 | Whittaker et al. |
| 5,423,823 A | 6/1995 | Schmieding |
| 5,423,860 A | 6/1995 | Lizardi et al. |
| 5,425,733 A | 6/1995 | Schmieding |
| 5,443,468 A | 8/1995 | Johnson |
| 5,443,482 A | 8/1995 | Stone et al. |
| 5,445,833 A | 8/1995 | Badylak et al. |
| 5,451,203 A | 9/1995 | Lamb |
| 5,454,811 A | 10/1995 | Huebner |
| 5,454,834 A | 10/1995 | Boebel et al. |
| 5,456,685 A | 10/1995 | Huebner |
| 5,458,601 A | 10/1995 | Young, Jr. et al. |
| 5,458,604 A | 10/1995 | Schmieding |
| 5,464,427 A | 11/1995 | Curtis et al. |
| 5,464,440 A | 11/1995 | Johansson |
| 5,470,334 A | 11/1995 | Ross et al. |
| 5,472,452 A | 12/1995 | Trott |
| 5,474,572 A | 12/1995 | Hayhurst |
| 5,480,403 A | 1/1996 | Lee et al. |
| 5,486,197 A | 1/1996 | Le et al. |
| 5,500,000 A | 3/1996 | Feagin et al. |
| 5,520,691 A | 5/1996 | Branch |
| 5,522,817 A | 6/1996 | Sander et al. |
| 5,522,844 A | 6/1996 | Johnson |
| 5,522,845 A | 6/1996 | Wenstrom, Jr. |
| 5,524,946 A | 6/1996 | Thompson |
| 5,527,342 A | 6/1996 | Pietrzak et al. |
| 5,540,718 A | 7/1996 | Bartlett |
| 5,549,613 A | 8/1996 | Goble et al. |
| 5,573,548 A | 11/1996 | Nazre et al. |
| 5,584,695 A | 12/1996 | Lal Sachdeva et al. |
| 5,584,835 A | 12/1996 | Greenfield |
| 5,593,425 A | 1/1997 | Bonutti et al. |
| 5,601,557 A | 2/1997 | Hayhurst |
| 5,603,716 A | 2/1997 | Morgan et al. |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,643,266 A | 7/1997 | Li |
| 5,643,320 A | 7/1997 | Lower et al. |
| 5,643,321 A | 7/1997 | McDevitt |
| 5,645,568 A | 7/1997 | Chervitz et al. |
| 5,645,588 A | 7/1997 | Graf et al. |
| 5,647,874 A | 7/1997 | Hayhurst |
| 5,649,963 A | 7/1997 | McDevitt |
| 5,662,658 A | 9/1997 | Wenstrom, Jr. |
| 5,671,695 A | 9/1997 | Schroeder |
| 5,674,224 A | 10/1997 | Howell et al. |
| 5,681,352 A | 10/1997 | Clancy, III et al. |
| 5,690,676 A | 11/1997 | DiPoto et al. |
| 5,699,657 A | 12/1997 | Paulson |
| 5,702,397 A * | 12/1997 | Goble et al. .................. 606/232 |
| 5,713,005 A | 1/1998 | Proebsting |
| 5,713,905 A | 2/1998 | Goble et al. |
| 5,733,307 A | 3/1998 | Dinsdale |
| 5,766,221 A | 6/1998 | Benderev et al. |
| 5,766,250 A | 6/1998 | Chervitz et al. |
| 5,769,894 A | 6/1998 | Ferragamo |
| 5,782,864 A | 7/1998 | Lizardi |
| 5,782,866 A | 7/1998 | Wenstrom, Jr. |
| 5,785,714 A | 7/1998 | Morgan et al. |
| 5,810,848 A | 9/1998 | Hayhurst |
| 5,814,070 A | 9/1998 | Borzone et al. |
| 5,824,011 A | 10/1998 | Stone et al. |
| 5,868,789 A | 2/1999 | Huebner |
| 5,885,294 A | 3/1999 | Pedlick et al. |
| 5,899,938 A | 5/1999 | Sklar et al. |
| 5,911,721 A | 6/1999 | Nicholson et al. |
| 5,918,604 A | 7/1999 | Whelan |
| 5,931,838 A | 8/1999 | Vito |
| 5,931,869 A | 8/1999 | Boucher et al. |
| 5,951,559 A | 9/1999 | Burkhart |
| 5,957,953 A | 9/1999 | DiPoto et al. |
| 5,964,764 A | 10/1999 | West, Jr. et al. |
| 5,964,783 A | 10/1999 | Grafton et al. |
| 5,980,558 A | 11/1999 | Wiley |
| 5,980,559 A | 11/1999 | Bonutti |
| 6,010,525 A | 1/2000 | Bonutti et al. |
| 6,027,523 A | 2/2000 | Schmieding |
| 6,045,573 A | 4/2000 | Wenstrom, Jr. et al. |
| 6,056,752 A | 5/2000 | Roger |
| 6,086,591 A | 7/2000 | Bojarski |
| 6,086,592 A | 7/2000 | Rosenberg et al. |
| 6,086,608 A | 7/2000 | Ek et al. |
| 6,099,530 A | 8/2000 | Simonian et al. |
| 6,099,568 A * | 8/2000 | Simonian et al. .......... 623/13.11 |
| 6,132,433 A | 10/2000 | Whelan |
| 6,132,437 A | 10/2000 | Omurtag et al. |
| 6,139,565 A | 10/2000 | Stone et al. |
| 6,146,408 A | 11/2000 | Bartlett |
| 6,152,928 A | 11/2000 | Wenstrom, Jr. |
| 6,156,039 A | 12/2000 | Thal |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,187,025 B1 | 2/2001 | Machek |
| 6,193,754 B1 | 2/2001 | Seedhom |
| 6,200,329 B1 | 3/2001 | Fung et al. |
| 6,203,572 B1 | 3/2001 | Johnson et al. |
| 6,221,107 B1 | 4/2001 | Steiner et al. |
| 6,231,592 B1 | 5/2001 | Bonutti et al. |
| 6,235,057 B1 | 5/2001 | Roger et al. |
| 6,241,747 B1 | 6/2001 | Ruff |
| 6,267,766 B1 | 7/2001 | Burkhart |
| 6,283,996 B1 | 9/2001 | Chervitz et al. |
| 6,296,659 B1 | 10/2001 | Foerster |
| 6,319,271 B1 | 11/2001 | Schwartz et al. |
| 6,371,124 B1 | 4/2002 | Whelan |
| 6,387,129 B2 | 5/2002 | Rieser et al. |
| 6,436,124 B1 | 8/2002 | Anderson et al. |
| 6,440,134 B1 | 8/2002 | Zaccherotti et al. |
| 6,451,030 B2 | 9/2002 | Li et al. |
| 6,482,210 B1 | 11/2002 | Skiba et al. |
| 6,508,830 B2 | 1/2003 | Steiner |
| 6,511,499 B2 | 1/2003 | Schmieding et al. |
| 6,517,578 B2 | 2/2003 | Hein |
| 6,527,795 B1 | 3/2003 | Lizardi |
| 6,533,802 B2 | 3/2003 | Bojarski et al. |
| 6,537,319 B2 | 3/2003 | Whelan |
| 6,540,750 B2 | 4/2003 | Burkhart |
| 6,544,281 B2 | 4/2003 | ElAttrache et al. |
| 6,551,343 B1 | 4/2003 | Tormala et al. |
| 6,553,802 B2 | 4/2003 | Jacob et al. |
| 6,554,862 B2 | 4/2003 | Hays et al. |
| 6,579,295 B1 | 6/2003 | Supinski |
| 6,585,730 B1 | 7/2003 | Foerster |
| 6,589,245 B1 | 7/2003 | Weiler et al. |
| 6,599,289 B1 | 7/2003 | Bojarski et al. |
| 6,616,694 B1 | 9/2003 | Hart |
| 6,620,329 B2 | 9/2003 | Rosen et al. |
| 6,623,524 B2 | 9/2003 | Schmieding |
| 6,626,910 B1 | 9/2003 | Hogues |
| 6,626,919 B1 | 9/2003 | Swanstrom |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,563 B2 | 11/2003 | Dreyfuss |
| 6,656,182 B1 | 12/2003 | Hayhurst |
| 6,682,549 B2 | 1/2004 | Bartlett |
| 6,685,728 B2 | 2/2004 | Sinnott et al. |
| 6,689,154 B2 | 2/2004 | Bartlett |
| 6,692,499 B2 | 2/2004 | Tormala et al. |
| 6,712,849 B2 | 3/2004 | Re et al. |
| 6,730,092 B2 | 5/2004 | Songer |
| 6,773,450 B2 | 8/2004 | Leung et al. |
| 6,780,190 B2 | 8/2004 | Maroney |
| 6,802,862 B2 | 10/2004 | Roger et al. |
| 6,833,005 B1 | 12/2004 | Mantas et al. |
| 6,840,953 B2 | 1/2005 | Martinek |
| 6,863,671 B1 | 3/2005 | Strobel et al. |
| 6,887,259 B2 | 5/2005 | Lizardi |
| 6,902,573 B2 | 6/2005 | Strobel et al. |
| 6,916,321 B2 | 7/2005 | TenHuisen et al. |
| 6,923,823 B1 | 8/2005 | Bartlett et al. |

| | | |
|---|---|---|
| 6,923,824 B2 | 8/2005 | Morgan et al. |
| 6,972,027 B2 | 12/2005 | Fallin et al. |
| 6,986,781 B2 | 1/2006 | Smith |
| 7,097,654 B1 | 8/2006 | Freedland |
| 7,491,217 B1 * | 2/2009 | Hendren et al. ............ 606/232 |
| 7,500,983 B1 | 3/2009 | Kaiser et al. |
| 7,695,503 B1 | 4/2010 | Kaiser et al. |
| 2001/0014825 A1 | 8/2001 | Burke et al. |
| 2001/0037131 A1 | 11/2001 | Schmieding et al. |
| 2001/0037153 A1 | 11/2001 | Rockwood et al. |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013608 A1 | 1/2002 | ElAttrache et al. |
| 2002/0099411 A1 | 7/2002 | Bartlett |
| 2002/0111653 A1 | 8/2002 | Foerster |
| 2002/0120292 A1 | 8/2002 | Morgan |
| 2002/0128684 A1 | 9/2002 | Foerster |
| 2002/0147463 A1 | 10/2002 | Martinek |
| 2002/0161401 A1 | 10/2002 | Steiner |
| 2002/0161439 A1 * | 10/2002 | Strobel et al. ............. 623/13.14 |
| 2002/0173788 A1 | 11/2002 | Bojarski et al. |
| 2002/0188298 A1 | 12/2002 | Chan |
| 2003/0023268 A1 | 1/2003 | Lizardi |
| 2003/0088272 A1 | 5/2003 | Smith |
| 2003/0120309 A1 | 6/2003 | Colleran et al. |
| 2003/0130694 A1 | 7/2003 | Bojarski et al. |
| 2003/0135239 A1 | 7/2003 | Gabriel et al. |
| 2003/0135963 A1 | 7/2003 | Holbrook et al. |
| 2003/0167072 A1 | 9/2003 | Oberlander |
| 2003/0167090 A1 | 9/2003 | Chervitz et al. |
| 2003/0176865 A1 | 9/2003 | Supinski |
| 2003/0176919 A1 | 9/2003 | Schmieding |
| 2004/0015171 A1 | 1/2004 | Bojarski et al. |
| 2004/0092936 A1 | 5/2004 | Miller et al. |
| 2004/0098051 A1 | 5/2004 | Fallin et al. |
| 2004/0138706 A1 | 7/2004 | Abrams et al. |
| 2004/0147929 A1 | 7/2004 | Biedermann et al. |
| 2004/0153153 A1 | 8/2004 | Elson et al. |
| 2004/0162579 A1 | 8/2004 | Foerster |
| 2004/0243178 A1 | 12/2004 | Haut et al. |
| 2005/0038426 A1 | 2/2005 | Chan |
| 2005/0096696 A1 | 5/2005 | Forsberg |
| 2005/0096697 A1 | 5/2005 | Forsberg et al. |
| 2005/0107828 A1 | 5/2005 | Reese |
| 2005/0119531 A1 | 6/2005 | Sharratt |
| 2005/0222618 A1 | 10/2005 | Dreyfuss et al. |
| 2005/0222619 A1 | 10/2005 | Dreyfuss et al. |
| 2005/0267479 A1 | 12/2005 | Morgan et al. |
| 2005/0277961 A1 | 12/2005 | Stone et al. |
| 2005/0283156 A1 | 12/2005 | Schmieding et al. |
| 2005/0283158 A1 | 12/2005 | West |
| 2006/0079904 A1 | 4/2006 | Thal |
| 2007/0016305 A1 | 1/2007 | Chudik |
| 2007/0225719 A1 | 9/2007 | Stone et al. |
| 2008/0082127 A1 | 4/2008 | Stone et al. |
| 2008/0082128 A1 | 4/2008 | Stone |
| 2008/0161852 A1 | 7/2008 | Kaiser et al. |
| 2009/0204146 A1 | 8/2009 | Kaiser et al. |
| 2010/0256677 A1 | 10/2010 | Albertorio et al. |
| 2010/0268273 A1 | 10/2010 | Albertorio et al. |
| 2010/0312341 A1 | 12/2010 | Kaiser et al. |

FOREIGN PATENT DOCUMENTS

| | | |
|---|---|---|
| DE | 2747312 | 4/1979 |
| DE | 2818254 | 10/1979 |
| DE | 4127550 | 2/1993 |
| EP | 0 129 442 | 12/1984 |
| EP | 0 172 130 | 2/1986 |
| EP | 0 241 240 | 10/1987 |
| EP | 0 241 792 | 10/1987 |
| EP | 0 260 970 | 3/1988 |
| EP | 0270704 | 6/1988 |
| EP | 0 282 789 | 9/1988 |
| EP | 0 317 406 | 5/1989 |
| EP | 0340159 | 11/1989 |
| EP | 0 346 183 | 12/1989 |
| EP | 0 349 173 | 1/1990 |
| EP | 0 374 088 | 6/1990 |
| EP | 0409364 | 1/1991 |
| EP | 0415915 | 3/1991 |
| EP | 0 451 932 | 10/1991 |
| EP | 0 464 480 | 1/1992 |
| EP | 0502509 | 9/1992 |
| EP | 0520177 | 12/1992 |
| EP | 520177 | 12/1992 |
| EP | 0 497 079 | 6/1993 |
| EP | 0 546 726 | 6/1993 |
| EP | 0574707 | 12/1993 |
| EP | 0 582 514 | 2/1994 |
| EP | 0591991 | 4/1994 |
| EP | 0 627 203 | 12/1994 |
| FR | 2 622 790 | 5/1989 |
| FR | 2 655 840 | 6/1991 |
| FR | 2682867 | 4/1993 |
| FR | 2 687 911 | 9/1993 |
| FR | 2 688 689 | 9/1993 |
| FR | 2 704 140 | 10/1994 |
| GB | 1413477 | 11/1975 |
| GB | 1485681 | 9/1977 |
| GB | 2 118 474 | 11/1983 |
| GB | 2 227 175 | 7/1990 |
| GB | 2 253 147 | 9/1992 |
| JP | 5300917 | 11/1993 |
| WO | WO 86/03666 | 7/1986 |
| WO | WO-8901767 | 3/1989 |
| WO | WO 89/09030 | 10/1989 |
| WO | WO 89/10096 | 11/1989 |
| WO | WO 90/08510 | 8/1990 |
| WO | WO 92/03980 | 3/1992 |
| WO | WO-9314705 | 8/1993 |
| WO | WO-9529637 | 11/1995 |
| WO | WO-9532670 | 12/1995 |
| WO | WO 96/29029 | 9/1996 |
| WO | WO 98/12991 | 4/1998 |
| WO | WO 98/12992 | 4/1998 |
| WO | WO-9812992 | 4/1998 |

OTHER PUBLICATIONS

"Technique for ACL Reconstruction with Acufex Director Drill Guide and Endobutton CL," by Thomas D. Roseberg, copyright 1999 Smith & Nephew.

"SE Graft Tensioning System Surgical Technique," Linvatec Corporation copyright 2003, 2004.

Bio-Intrafix (TCP/PLA) & Intrafix, Tibial Soft Tissue Fasteners, by DePuy Mitek, 6 sheets, (date unknown).

* cited by examiner

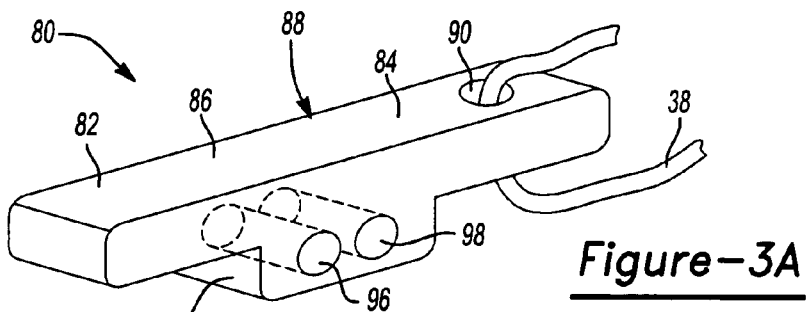
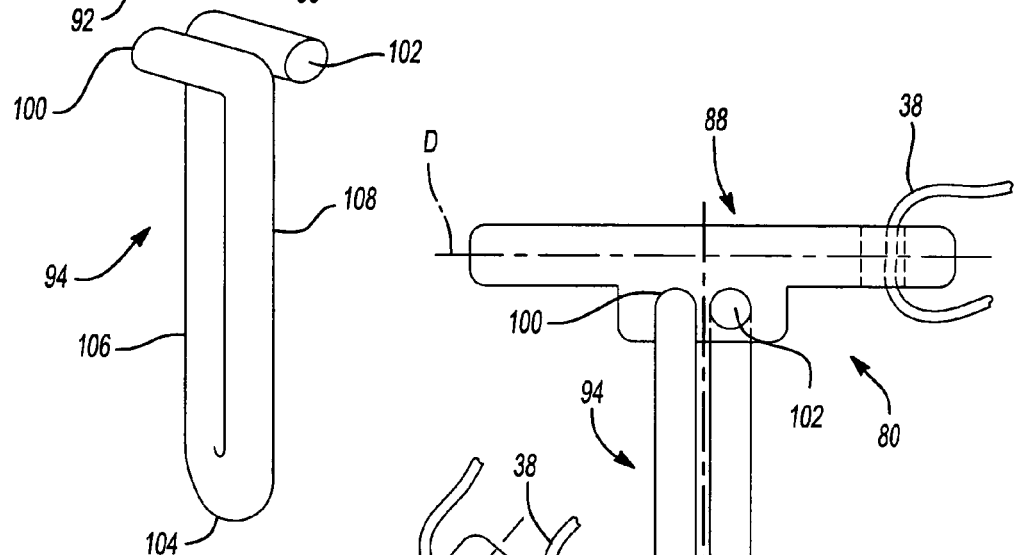
*Figure-3A*
*Figure-3B*
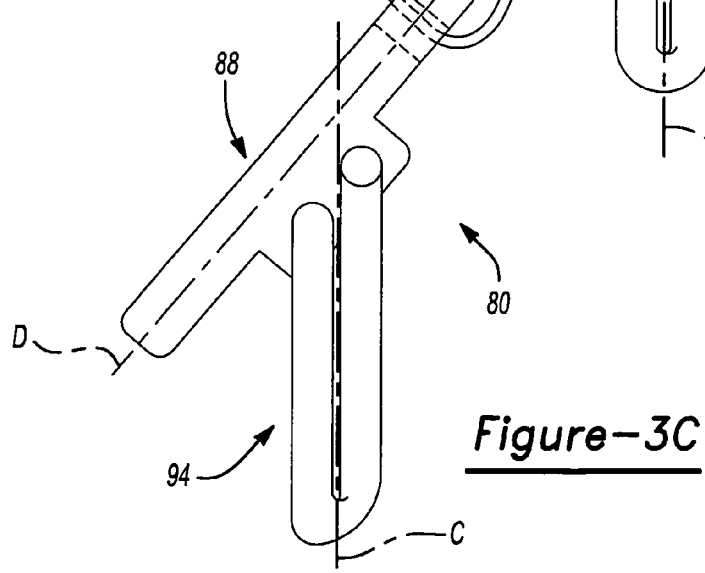
*Figure-3C*

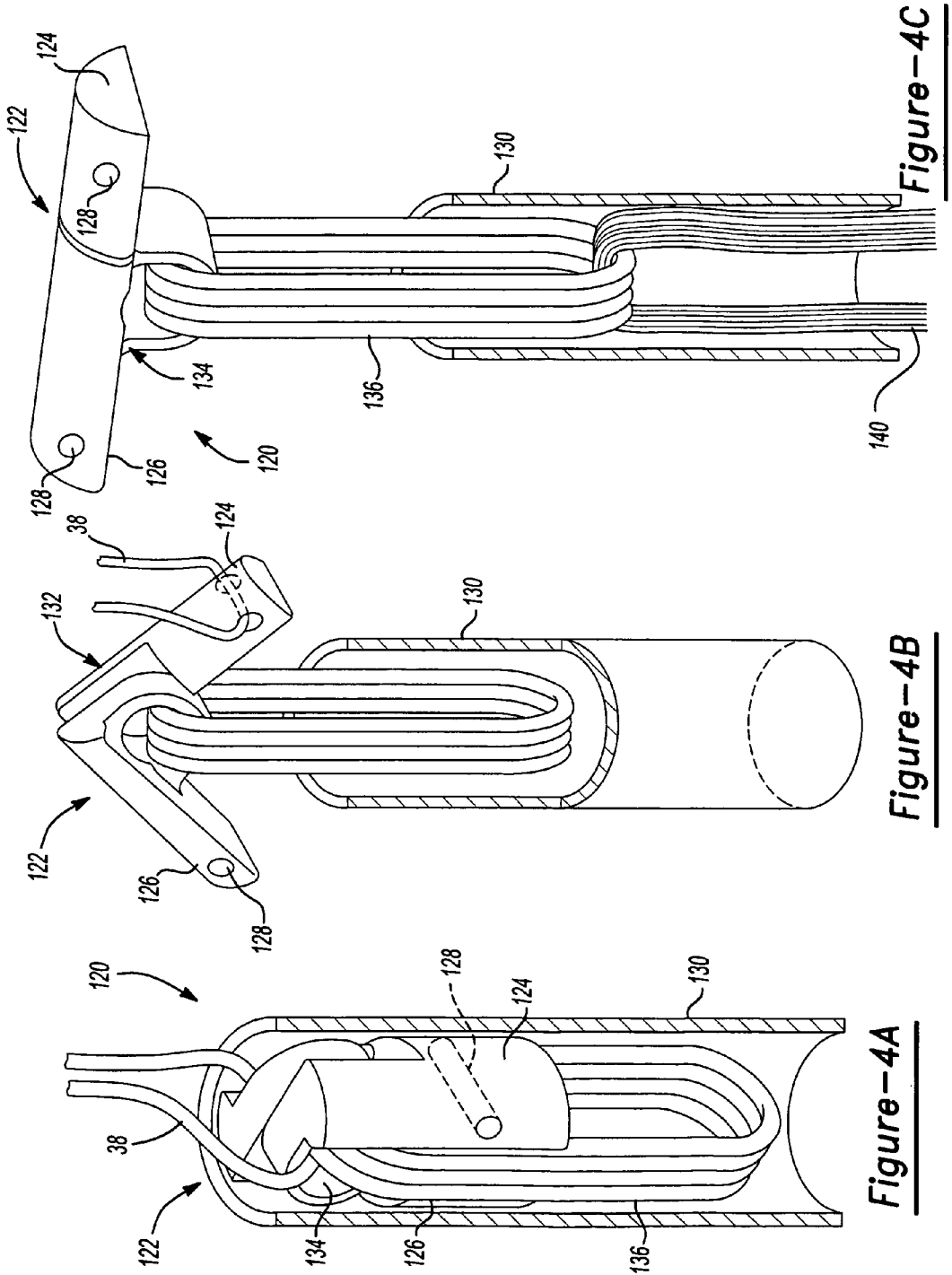

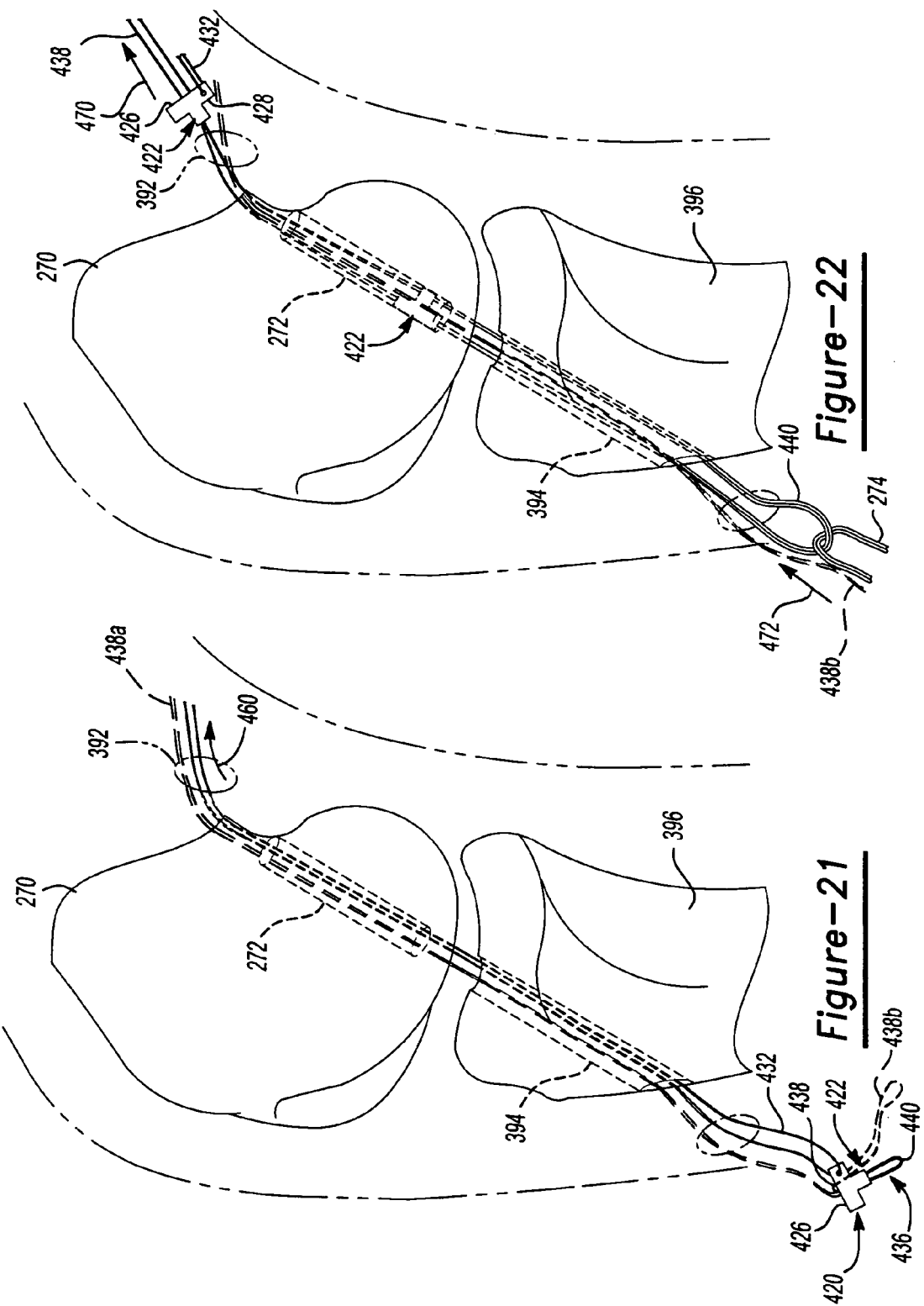

METHOD AND APPARATUS FOR SOFT TISSUE FIXATION

CROSS-REFERENCE TO RELATED APPLICATIONS

This application is a continuation-in-part of U.S. patent application ser. No. 11/203,481, filed on Aug. 12, 2005 now U.S. Pat. No. 7,819,898, which is a continuation-in-part of U.S. patent application Ser. No. 10/864,900, filed on Jun. 9, 2004 and issued Mar. 10, 2009 as U.S. Pat. No. 7,500,983. The disclosures of the above applications are incorporated herein by reference.

FIELD

The teachings relate generally to orthopedic procedures; and relate particularly to orthopedic procedures for interconnecting soft tissue to a bony portion of an anatomy.

BACKGROUND

In an anatomy, such as a human anatomy, various soft tissue portions are interconnected with various bony portions. For example, a tendon may interconnect a selected muscle group with a selected portion of the anatomy. Similarly, a ligament may interconnect two bony portions. For example, the anterior cruciate ligament interconnects a portion of the tibia with a portion of the femur. Although the natural and healthy anatomy generally is able to support the various portions of the anatomy with the natural ligaments and tendons, and other selected soft tissues, injury, age, or other circumstances may cause weakening or breaking of various soft tissue portions.

For example, a strain, other injury, or disease may weaken various soft tissue portions, such as the anterior cruciate ligament (ACL). The breaking or weakening of the tissue may require the tissue to be reconnected or replaced with various autografts or xenografts that may be made of natural or synthetic materials. These various materials are generally interconnected with selected portions of the anatomy using screws or other similar friction or obstruction holding devices.

Though various procedures and instruments may allow for interconnection of soft tissue with selected bony portions, it may be desirable to perform a procedure substantially percutaneously or through a small incision or in less time. Generally, the screws or the obstruction devices must be driven into the selected bony portion to hold the selected soft tissue in the appropriate location. The procedure must be planned and executed in a particular manner to insure that appropriate fixation of the soft tissue to the selected bony portion. Therefore, it may be desirable to provide an instrument and method that allows for a substantially quick implantation or connection of a selected soft tissue graft or soft tissue portion to a selected bony portion.

SUMMARY

A device for connecting or holding a soft tissue graft relative to a selected anatomicat portion such as a bone portion. An anchor may be provided that is operably interconnected with a selected portion of the graft and the anchor may anchor the connection portion to the selected bony portion. For example, the anchor portion may be passed through a bore and manipulated to hold the soft tissue graft relative to the bore by providing an interference fit with a portion of the bone next to or relative to the bore. The anchor may be formed as substantially a single piece or may be an assembly of a plurality of pieces, such that the anchor may pass through the bore and may be manipulated to interfere with passing in an opposite direction through the bore again. The anchor may also be passed or interact with various other portions to assist in positioning and deploying of the anchor.

In addition, a portion of the instrument or fixation device may include a spreading or spacer portion that may hold apart selected portions of a selected graft during an implant procedure and after the implantation has occurred. The spacer may allow a reduction of a local stress on a selected implant after implantation and may ease implanting of the implant. In addition, a spacer may allow for proper positioning of various portions of the implant during the procedure and insure that the implant is kept at a proper spacing after implantation. Moreover, a spacer may assist in allowing for natural adhesion to selected portions of the anatomy.

According to various embodiments a soft tissue connection assembly may be operable to hold a soft tissue graft near a select portion of an anatomy. The assembly may include an anchor member to selectively engage the selected portion of the anatomy. The anchor member may generally define a lever arm and an engaging portion extending from the lever arm. The assembly may also include a positioning member operable to interact with the anchor member to move the anchor member to a deployed orientation. The soft tissue interconnects with the engaging portion to be substantially held in a selected position relative to the selected portion of the anatomy.

According to various embodiments an anchor member to selectively anchor a graft relative to a selected portion of an anatomy is disclosed. The anchor may define a lever arm extending along a first axis between a first end and a second end and an activation region defined by the lever arm. The member may also include a resiliently flexible member operable to assist in moving the lower arm. The lever arm is selectable between an activated position and a non-activated position with the activation region.

According to various embodiments a method of fixing a graft in a selected region of an anatomy with an anchor member is disclosed. The method may include forming a bore in the selected region of the anatomy thereby defining an interior surface within the bore and an exterior surface outside of the bore. A graft may be associated with the flexible member and the anchor member may be passed through a selected portion of the bore to a first position in a first orientation. A positioning member may be held in a first position when the anchor is in the first orientation and the anchor member may be moved at least in part with the positioning member to a second position thereby selectively engaging the exterior surface. Also, the graft may be held in a selected position.

According to various embodiments an anchor assembly for anchoring a graft in an anatomy is disclosed. The anchor assembly can include an anchor body member having a main body operable to be positioned in the anatomy and an edge extending from the anchor body operable to engage the anatomy and to resist movement a the anchor body into the anatomy. A selectable graft engagement member and can cooperate with an activation member that is operably connected with the selectable graft engagement member to select a size of the graft engagement member.

According to various embodiments an anchor assembly to anchor a graft in an anatomy is disclosed. The anchor assembly can include an anchor body defining a passage. A flexible member can extend through the passage defined by the anchor body. The flexible member can include a graft engaging portion and a selection portion. The selection portion can be used to select a size of the graft engaging portion.

According to various embodiments a method of holding a graft in a selected position relative to a portion of an anatomy with an anchor is disclosed. The method can include forming a bore in a bone and positioning the anchor relative to the bone. A graft engaging member can be passed through the bore and can a graft. The graft can be moved through the bore with the graft engaging member by moving the graft engaging member with an activation member.

Further areas of applicability will become apparent from the detailed description provided hereinafter. It should be understood that the detailed description and various embodiments are intended for purposes of illustration only and are not intended to limit the scope of the teachings.

BRIEF DESCRIPTION OF THE DRAWINGS

The present description and appended claims will become more fully understood from the detailed description and the accompanying drawings, wherein:

FIG. 3A is an exploded view of an anchor according to various embodiments;

FIG. 3B is an assembled view of the anchor of FIG. 3A in an activated position;

FIG. 3C is an elevational view of the anchor of FIG. 3A in an activated position;

FIG. 4A is an anchor assembly according to various embodiments in an unactivated position;

FIG. 4B is the anchor of FIG. 4A in a partially activated position;

FIG. 4C is the anchor of FIG. 4A in an activated position;

FIGS. 21-23 are environmental views of a use of an anchor assembly according to various embodiments.

DETAILED DESCRIPTION OF VARIOUS EMBODIMENTS

The following description of various embodiments is merely exemplary in nature and is in no way intended to limit the invention, its application, or uses. Although the following description may relate to providing a soft tissue anchor relative to a femur, such as for an anterior cruciate ligament (ACL) fixation, the various apparati and methods may be used for a plurality of procedures. For example, the various instruments may be used to affix or hold a hamstring, Achilles tendon allograft, other soft tissue, or any other appropriate portion. In addition, although various embodiments may be illustrated to be interconnected with a selected graft using a flexible strand, such as a suture, it will be understood that a graft may be affixed directly to an implant member. Therefore, it will be understood that the following description is merely exemplary of various embodiments and is not intended to be limiting.

Figure 1A:
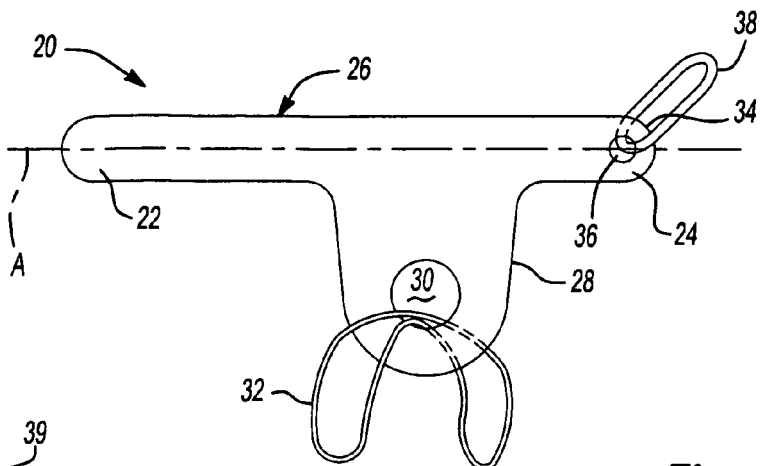
FIG. 1A is a side plan view of an anchor according to various embodiments.

With reference to FIG. 1A, an anchor 20 may be provided. The anchor 20, according to various embodiments, may be used to anchor any appropriate portion such as a soft tissue, suture, or the like. The anchor 20 may include a first flange or portion 22 extending in a first direction and a second flange or portion 24 extending in a second direction. The first flange 22 and the second flange 24 generally interconnect to form a lever or arm portion 26 of the anchor 20. The arm portion 26, as described further herein, may be maneuvered to engage a selected portion of an anatomy to hold a selected graft or portion relative to the anatomy.

Extending from the arm portion 26 is a holding or engaging portion 28. The engaging portion 28 may be positioned relative to the arm portion 26 in any appropriate manner. For example, the first flange 22 may have a length that is greater than the second flange 24, therefore, the soft tissue anchor portion 28 may be formed closer to a selected end than another selected end of the anchor 20.

The engaging portion 28 may also include a fixation area or portion 30. The fixation portion 30 may be a bore or passage provided through the soft tissue anchor portion 28. The passage 30 may allow a selected portion of a soft tissue graft, or any other appropriate implant to pass through. Alternatively, a suture or strand portion 32, such as a loop, a plurality of loops, or a link may pass through the passage 30 to engage the anchor 20 and interconnect the soft tissue graft or portion. Therefore, the suture loop 32 that may be a substantially continuous suture loop, may be provided through the passage 30.

The lever arm 26 of the anchor 20 may also be formed in any appropriate manner. For example, the lever arm 26 may extend substantially along a selected axis A and be substantially planar. Alternatively, the lever arm 26 may extend along any appropriate radius to define a substantially curved lever arm portion. It will be understood, therefore, that the lever arm portion 26 may be formed in any appropriate manner for selected applications.

An engagement or activation area 34 may extend from a portion of the first flange 22 or the second flange 24. The activation area may include a passageway 36 that may be formed in the portion of the second flange 24. An activation or passing member, such as a suture portion 38, may also pass through the activation bore 36 to assist in positioning the anchor 20. The suture portion 38 will be understood to be any appropriate portion, such as any appropriate flexible strand suture portion, or may also include a rigid member to interconnect with the activation portion of the anchor 20. Nevertheless, the suture portion 38 may be passed through a selected portion of anatomy to move the anchor 20 through the selected portion of the anatomy, as described in detail herein. It will also be understood that the suture portion 38 may not be necessary and the anchor 20 may include a portion that may act as a portion to pull the anchor 20 through a selected portion of the anatomy. For example, a generally integrally formed portion may extend from the anchor 20 and near the activation region 30 that may or may not be frangible and may be detached from the anchor 20 at a selected time. Therefore, the suture portion 38 may not be necessary and may be omitted in lieu of providing another portion that may add to move the anchor 20 in a selected fashion.

Figure 1B:
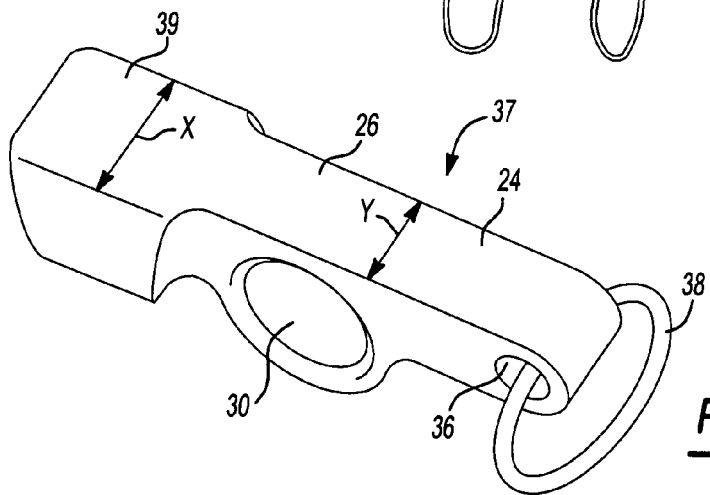
FIG. 1B is a perspective view of an anchor according to various embodiments.

With reference to FIG. 1B, an anchor 37, according to various embodiments, is illustrated. The anchor 37 may be similar to the anchor 20 and similar numerals are used to reference similar portions. For example, the anchor 37 may include a first flange portion 39 that includes at least a first dimension X greater than a dimension Y of the second flange 24. As discussed above, the first flange 39 and the second flange portion 24 may define a lever or arm portion 26. Defining at least a portion of the lever arm portion 26 is the fixation portion 30. The fixation portion 30 may include a dimension that at least is partly defined by the lever arm 26. Although a portion of the fixation portion 30 may extend beyond the arm 26, the arm 26 may define at least a portion of the fixation portion 30. In addition, an activation portion or bore 36 may be defined by a portion of the arm 26, such as a portion of the second flange 24. As discussed above, an activation member 38 may be provided to activate the anchor 37 at an appropriate time.

Figure 2A:
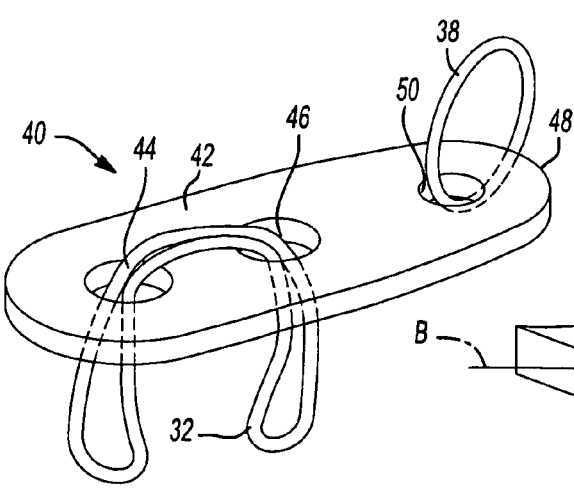
FIG. 2A is a top perspective view of an anchor according to various embodiments.

With reference to FIG. 2A, an anchor 40 according to various embodiments may be provided that generally includes a planar body or portion 42. Formed through the body 42 may be a soft tissue anchor portion that may include a first bore 44 and a second bore 46. The soft tissue graft or a selected portion, such as a suture loop 32, may be provided through the bores 44, 46 to engage a selected soft tissue portion. In addition, the anchor 40 may include a activation region 48 that may include a activation bore 50, similar to the activation bore 36 of the anchor 20. Similarly, the suture 38 or other appropriate portion may extend through the activation bore 50 to assist in passing the anchor 40 through a selected portion and manipulating the anchor 40 in a selected manner. Therefore, the anchor 40 may be provided, such that it will pass through a selected portion of the anatomy, as described further herein, and manipulated with the suture loop 38 to assist in fixing a selected soft tissue graft with the anchor 40.

Figure 2B:
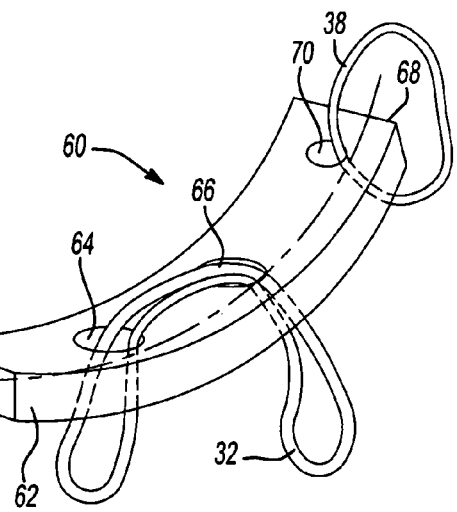
FIG. 2B is a top perspective view of an anchor according to various embodiments.

With reference to FIG. 2B, an anchor 60 may be provided including a substantially arcuate body portion 62 that extends along an arc B of any selected radius. Similar to the anchor 40, the anchor 60 may include a soft tissue attachment portion, including a first bore 64 and a second bore 66. The suture strand or loop 32 may pass through the bores 64, 66 to engage a portion of soft tissue or a portion of soft tissue may engage the bore 64, 66. Nevertheless, the anchor 60 may be used to fix a selected portion of soft tissue relative to a portion of anatomy, or any other appropriate purpose.

The anchor 60 may also include a activation region 68 that may define a activation bore 70, similar to the bore 50 of the anchor 40. Again, similar to the anchor 40, the suture loop 38 may be passed through the bore 70 to be used to manipulate the anchor 60 in a selected manner during a procedure. Nevertheless, according to various embodiments, a portion may extend from the anchor 60 that is not necessarily included as a suture loop 38. Therefore, it will be understood that providing the suture loop 38 is merely exemplary.

Further, it will be understood that an anchor need not be formed as a single member. In addition to being formed as a single member, the anchor may be formed to include any appropriate geometry, shape, size, or the like. Therefore, the anchor need not include simply straight or curved portions or include a portion that extends from a portion of the anchor to engage the implant, but may be formed in any appropriate manner. It will be understood that the anchor may be passed through a selected portion of the anatomy in a first manner or condition and then manipulated to a second manner or position to assist in positioning the anchor in a selected position to perform the necessary tasks.

With reference to FIGS. 3A-3C, an anchor 80 according to various embodiments is illustrated. The anchor 80 may include a first flange or portion 82 extending in a first direction and second flange or portion 84 extending in a second direction from a central region 86. The arms 82 and 84 define a activation portion or member 88 of the anchor 80 as discussed herein. The lever arm portion 88 may be maneuvered, as discussed herein, to engage a selected portion of anatomy to hold a graft or other portion relative to a selected portion of the anatomy.

Formed in the second arm portion 84 is a activation bore 90 through which the activation suture 38 may be passed. As described herein, the activation suture 38 may be used to position the anchor 80 in a selected position and manipulate or maneuver the anchor from an unactivated to an activated position, thereby allowing the lever arm portion 88 to abut a selected portion of the anatomy and hold the anchor 80 in a selected position.

Defined near the fulcrum or central area 86 is an engaging portion 92. The engaging portion 92 may engage a graft engaging member or portion 94. The graft engaging portion 94 may be formed of a selected material, as described herein. The engaging region 92 may include a first bore 96 and a second bore 98. The bores 96, 98 may engage selected portions of the graft engaging section 94 such as first region 100 and a second region 102.

The graft engaging member 94 generally defines a substantially U or curved portion 104 from which extends a first extending portion 106 and a second extending portion 108. The first extending portion 106 extends to the first engaging member 102 while the second engaging portion 108 extends to the first engaging portion 100. Each of the engaging portions 100, 102 may engage a selected one of the bore 96, 98.

With particular reference to FIG. 3B, in an activated or neutral position, the anchor 80 includes the lever arm 88 at a generally perpendicular position relative to the graft engaging portion 94. The graft engaging portion 94 may define an axis C that is generally perpendicular to an axis D of the lever arm 88. Therefore, in the neutral or unactivated position, the lever arm 88 does not position or apply a substantial amount of stress to the graft engaging portion 94. As illustrated, a first engaging portion 100 and a second engaging portion 102 are passed through or engage a selected one of the bores 96, 98. In this way, the lever arm 88 is interconnected with the graft engaging portion 94 by both of the engaging portions 100, 102 of the graft engaging portion 94.

With particular reference to FIG. 3C, in an activated position, the activation suture 38 may apply a force to the lever arm 88 such that the lever arm 88 may be positioned or moved to an angle relative to the graft engaging portion 94. The axis D of the lever arm is generally positioned at an angle having an internal angle of less than 90° relative to the axis C of the graft engaging portion. In this way, a distance or width defined by the anchor 80 is less than the length of the lever 88 to allow for the anchor 80 to be passed through a selected portion of the anatomy.

The graft engaging member 94 may be formed of any selected material that may be moved from a first position to a second position and allowed to regain its first position or orientation substantially after the removal of a selected force. For example, the graft engaging member 94 may be formed of a wire of a selected material, such as a shape memory material including the material known as Nitinol™. It will be understood, however, that a shape memory material may be any appropriate material that may include a first shape, be deformed to a second, and substantially re-obtain the first shape. Therefore, shape memory materials may include, but are not limited to, metals, metal alloys, polymers, strands, natural and synthetic materials, or the like. The shape memory material may include a first selected shape or orientation which is generally maintained by the material and may be returned to or maintained by the material after deforming the material to a second shape or orientation.

As illustrated in FIG. 3C, the activation arm 88 may disorientate or move the graft engaging portion 94 into a second portion while the graft engaging portion 94 may re-obtain its first orientation, just as that illustrated in FIG. 3B, after the activation arm 88 has been released. Therefore, the graft, as discussed herein, may be held relative to a selected portion of the anatomy with the anchor 80 without substantially binding the graft in the graft engaging portion 94. The graft engaging portion 94 may be any appropriate substance such as a wire, plastic thread, filament, suture, or the like.

With reference to FIGS. 4A-4C, an anchor 120 according to various embodiments is illustrated. The anchor 120 may include an activation or lever portion 122 that generally includes a first arm portion 124 and a second arm portion 126. Defined in either the first or second arm portion, and illustrated in the first arm portion 124, is an activation bore 128 that may be formed in any appropriate orientation through either of the first arm position 124 or the second arm position 126. The activation bore 128 may be interconnected with the activation suture 38. Alternatively, the activation suture 38 may be positioned relative to any portion of the anchor 120. For example, the activation suture 38 may be interconnected with a sleeve 130 that substantially surrounds the lever arm 120. The lever portion 122 generally includes a central axle or rotation area about which the first arm 124 and the second arm 126 may rotate.

With particular reference to FIG. 4B, and described further herein, the first arm 124 may rotate about the axle area 132 relative to the second arm 126. This may allow the lever arm portion 122 to be moved from an unactivated to an activated position and allow it to selectively engage a selected portion of the anatomy. The axle portion 132 may be formed in any appropriate manner. For example, a portion of the first arm 124 may extend into a portion of the second arm 126 yet be substantially movable relative thereto. Therefore, the arm portions 124, 126 define an integral axial portion thereby not requiring a separate axle member. Nevertheless, it will be understood that an axle member may be provided in both the first arm and the second arm 124, 126 so that the arms 124, 126 may rotate relative to the axle portion to allow for movement of the first arm 124 relative to the second arm 126.

Nevertheless, a bore or opening 134 may be provided between the first arm 124 and the second arm 126 generally near the axle region 132 to allow for the passing of a suture 136 or similar apparatus. The suture 136 may allow a graft to be engaged by the anchor 120 to be held by the anchor in a selected position.

During insertion of the anchor 120, the activation member 122 and the suture loops 136 may be positioned within a sleeve or tube 130. It will be understood that the sleeve 130 is not necessary to position the anchor 120 but might be provided for various reasons such as positioning the graft, positioning the anchor and other appropriate reasons relative to the selected portions of the anatomy.

Nevertheless, as the anchor 120 is passed through a selected portion of the anatomy, the sleeve 130 may be stopped according to appropriate means in a selected area. Therefore, as illustrated in FIG. 4B, as the lever portion 122 is moved between an unactivated and an activated position, the lever 122 is substantially removed from the sleeve 130. This allows the first arm 124 to move relative to the second arm member 126 and vice versa while being substantially free of the obstruction of the sleeve 130. Nevertheless, also during moving the anchor 120 into a selected position, the sleeve 130 may assist in holding the arm portions 124, 126 of the lever portion 122 in a selected orientation.

With reference to FIG. 4C, once the anchor 120 including the lever arm 122 are positioned in a selected orientation, the lever portion 122 is in a substantially activated position such that the first arm 124 is substantially aligned and in a single axis with a second lever arm 126. As discussed above, this may be performed by substantially rotating about a central axle area 130, the first arm 124 relative to the second arm 126 and vice versa. The suture portion 136 extends from the lever portion 122 and may be positioned within the sleeve 130. A graft 140 that may be positioned over the suture member 136 may also extend through a portion of the sleeve 130 for positioning the graft 140 in a selected orientation. This allows the anchor 120 to be positioned in a selected portion of the anatomy and manipulated from the unactivated position to the activated position, particularly shown in FIG. 4C.

Figure 5A:
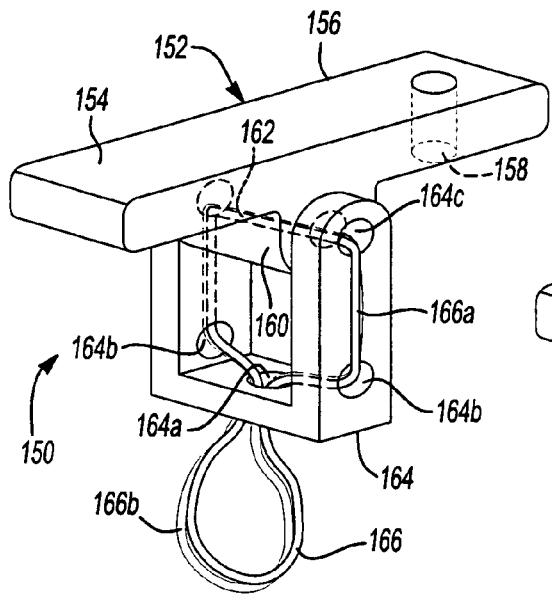
FIG. 5A is a perspective view of an anchor according to various embodiments.

With reference to FIG. 5A, an anchor 150, according to various embodiments, may include a activation portion 152 that includes a first arm portion 154 and a second arm portion 156. Defined in a selected arm portion, such as the second arm portion 156, may be a activation bore 158. As discussed above, an appropriate member, such as the activation suture 38, may be passed through the activation bore 158 to move the activation or lever section 152 from a first position or unactivated position to an activated position. The lever arm 152 defines a central or fulcrum region 160 that includes a bore 162. Further, an extension member 164 may be interconnected with the bore 162 or the fulcrum region 160 with a selected suture member 166.

A suture member 166 may pass through a first or central bore 164A defined in a selected region of the extension member 164 and through a second set of bores 164b and again through a third set of bores 164c. Therefore, the suture member 166 may define a substantially figure "8" portion 166a that includes a first portion of the figure "8" 166a that substantially interconnects the lever arm 152 with the extension member 164. A second section of the suture portion 166b may be used to engage a selected graft portion for positioning relative to a selected portion of the anatomy. As discussed herein, the lever arm 152 may be moved to a selected portion of the anatomy in an unactivated position and moved to the activated position, substantially illustrated in FIG. 5A, to engage a selected portion of the anatomy. The first section of the suture portion 166a allows for the lever arm 152 to move relative to the extension member 164 and the graft extending from the second portion of the suture 166b.

Figure 5B:
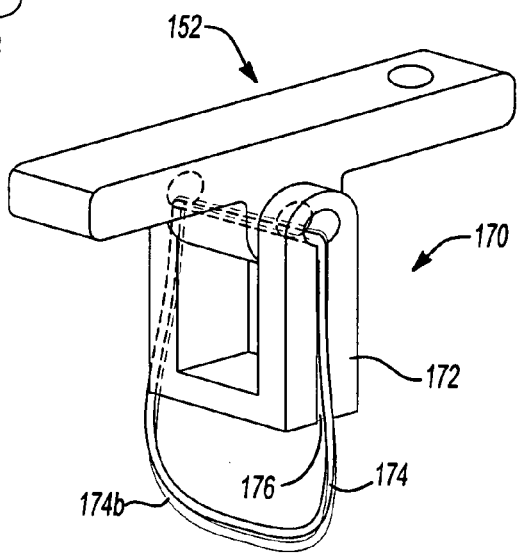
FIG. 5B is a perspective of an anchor according to various embodiments.

With reference to FIG. 5B, an anchor portion 170 includes a lever portion 152 substantially similar to the lever portion 152 illustrated in FIG. 5A, and will not be described in great detail here. Nevertheless, an extension member 172 extends from the lever arm portion 152 and is interconnected therewith with a suture portion 174. The suture portion defines substantially a continuous loop that includes a portion that extends through a bore defined in the extension member 172 and the fulcrum bore defined by the lever arm 152. A second section of the suture 174B extends and may engage a selected graft for implantation. As discussed above, a activation suture or portion may be used to pass the anchor 170 through a selected portion of the anatomy and used to move the lever arm 152 from an inactivated to an activated position. The suture 174 may be positioned in a groove or detent 176 to substantially limit an abrasion between the suture 174 and a portion of the anatomy.

Figure 6A:
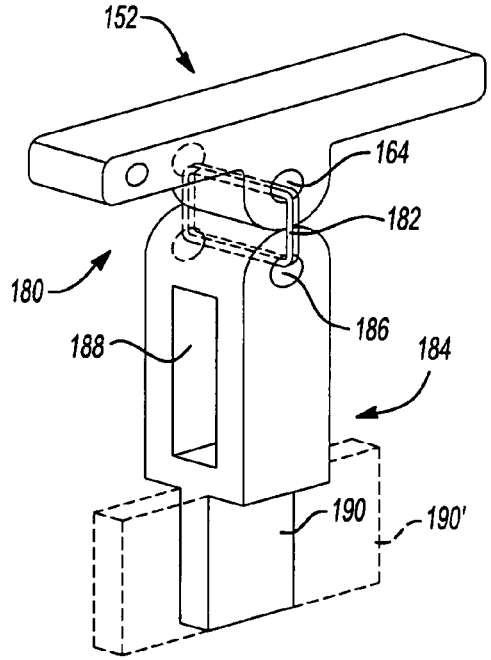
FIG. 6A is a perspective view of an anchor according to various embodiments.

With reference to FIG. 6A, an anchor assembly 180 according to various embodiments is illustrated. The anchor assembly 180 may include the lever arm 152 substantially similar to the lever arm 152 discussed above. A suture member 182 may be provided to interconnect the lever arm 152 with a spacer or extension member 184. The extension member 184 may define a bore 186 that allows the suture 182 to pass through and engage the bore 164 defined by the lever portion 152.

A selected graft may be passed through an opening or passage 188 defined by the extension spacer member 184 and allowed to drape through the opening 188 and over a spacer portion 190 of the extender spacer 184. The spacer portion 90 may be provided in any appropriate size, dimension, geometry, or the like. For example, as illustrated in phantom in FIG. 6A, the spacer portion 190' may extend a distance beyond a dimension of the spacer member 184 otherwise defined by the portion including the opening 188. It will be understood that the spacer portion 190 may also be provided in any appropriate geometry to interact with the anchor 152 or a portion, such as a soft tissue portion, passed through the opening 188. Therefore, as discussed herein, stress on a particular area of the graft may be reduced and the spacer 190 may be used to position the graft adjacent a selected portion of the anatomy. Nevertheless, the interconnection suture 182 between the lever portion 152 and the extension spacer 184 may allow for the lever arm 182 to be moved relative to the extension spacer portion 184 such as with a activation suture or portion.

Figure 6B:
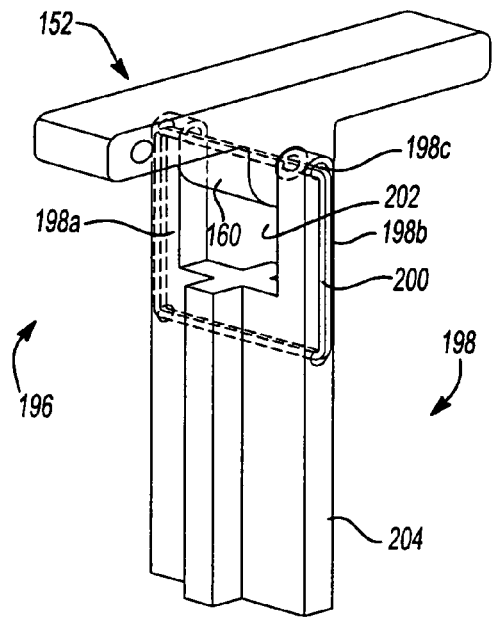
FIG. 6B is a perspective view of an anchor according to various embodiments.

With reference to FIG. 6B, an anchor 196, according to various embodiments, is illustrated. The anchor assembly 196 may include the lever portion 152, as discussed above. The anchor assembly 196 also includes a spacer extender portion 198 that may be interconnected with the lever portion 152 using a connection suture 200 or other appropriate mechanisms. The extender portion 198 includes a first arm 198A and a second arm 198B that may extend around a selected portion, such as the central or fulcrum region 116 of the lever portion 152 to allow the attachment suture 200 to interconnect the lever portion 152 and the spacer portion 198. The connection suture 200 may form a substantially continuous loop that passes through a plurality of bores defined by the spacer extender portion 198 to interconnect the lever portion 152 and the spacer portion 198.

Defined between the lever portion 152 and the spacer portion 198 is an opening or passage 202. The passage 202 may allow for positioning of a graft relative to the anchor assembly 196. The graft may drape through the opening 202 and be held in a relative position with the spacer portion 204 of the spacer extension portion 198. As discussed above and herein, the spacer portion may allow for positioning the graft in a selected position and substantially reducing a localized stress on the graft assembly.

As discussed above, the spacer extension portion 198 may include the spacer portion 204 formed in any appropriate shape, size, geometry, or the like. Therefore, as exemplary illustrated, the spacer portion 204 may be substantially cruciform in shape. The cruciform shape may extend and define a portion of the opening 202 or may extend only a portion of the length of the spacer portion 204. Therefore, it will be understood that the spacer portion 204 may be any appropriate shape, size, geometry, or other appropriate condition based upon selected parameters.

Figure 7A:
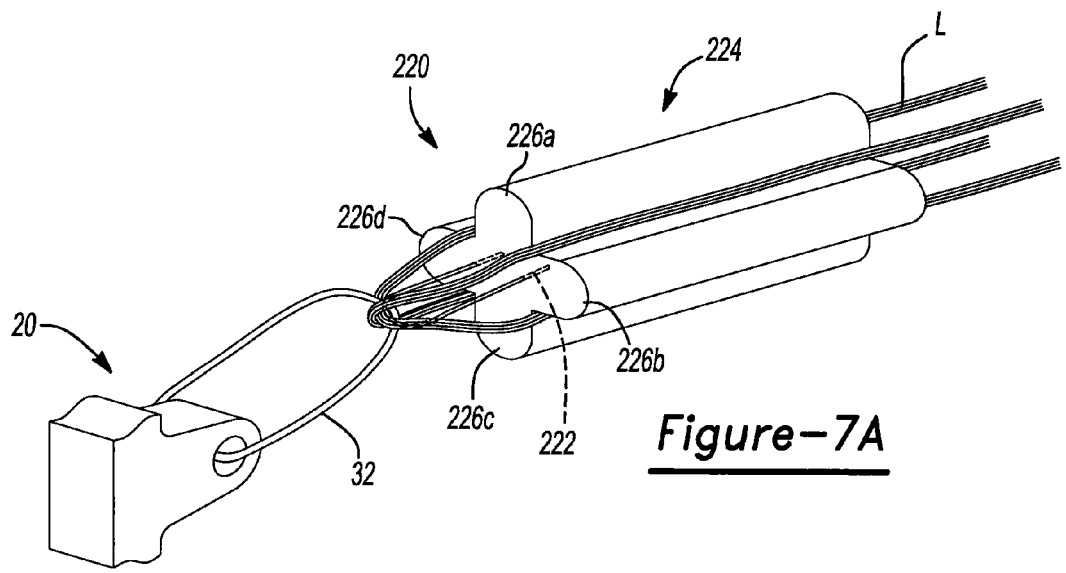
FIG. 7A-7C are top perspective views of spacers according to various embodiments.

With reference to FIG. 7A, a spacer or separator 220 is illustrated. The spacer 220 may be interconnected with the anchor 20, or any appropriate anchor or mechanism, with a connection loop or portion 222. The spacer 220 includes a spacer body 224 that may define a plurality of sections to assist in separating and spacing a portion of a soft tissue graft. For example, the body may define a plurality of ridges 226A, 226B, 226C, and 226D. The various ridges assist in holding portions of ligament implants, or other appropriate implants, apart for a selected period of time. For example, a plurality of strands of a soft tissue or graft, such as a ligament L, may be looped through the connecting suture 32 and allowed to pass over a portion of the spacer 220. The ligament L, which may also include any other appropriate soft tissue portion, may be provided over the spacer 220 to assist in implantation of the soft tissue. Each of the ridges 226A-226D assist in separating various portions of an implant and also define a major or exterior diameter of the spacer 220. Therefore, the spacer 220 may be used to hold an implant in an implanted position and also may assist in healing after the implantation. Nevertheless, the spacer 220 may be implanted with the anchor 20 in cooperation with the anchor 20 to assist in implanting a selected tissue portion.

Figure 7B:
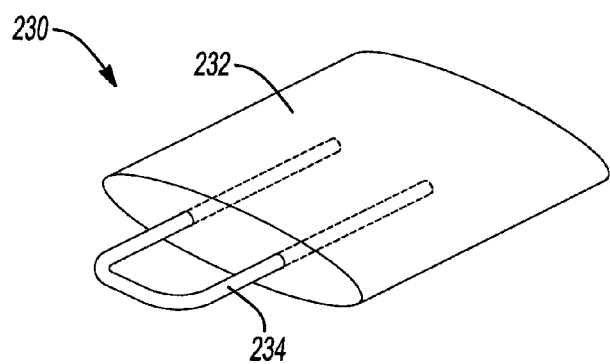

With reference to FIG. 7B, a spacer 230 according to various embodiments is illustrated. The spacer 230 includes a body portion 232 which may include or have extending therefrom an anchor attachment portion 234. The anchor attachment portion 234 may interconnect with the anchor 20, or any appropriate anchor portion, to assist in cooperating with a soft tissue implant to assist in implantation of the implant. As with the spacer 220, the soft tissue implant may be laid over the body portion 232 to assist in holding the soft tissue in a selected implant area and assist in healing after the implantation. It will be understood that the body portion 232 may be formed in any appropriate shape, geometry, size, and other proportions. For example, the body portion 232 may include a geometry or shape to assist in holding the soft tissue relative to a selected region of the body 232 and the implant area.

The attachment region 222 of the spacer 220 and 234 of the spacer 230 may be formed in any appropriate manner. Similarly, the body 224 of the spacer 220 and the body 232 of the spacer 230 may be formed of any appropriate material. For example, the body may be formed of a polymer, metal, or any appropriate biocompatible material. Therefore, the tissue attachment or the attachment region 222 and 234 may be formed of any appropriate material that may interconnect with the material of the body 224 and 232 in an appropriate manner. For example, the attachment area 222 or 234 may be formed of a flexible strand or suture material that may be molded into the body region 224 and 232 of the respective spacers 220 and 230. Alternatively, the attachment portions 232 and 234 may be any other appropriate portion that may be interconnected with the body portions 234 and 232 of the respective anchors 220 and 230. Therefore, the attachment portion 222 and 234 may be welded or otherwise affixed to the body portions 224 and 232.

Figure 7C:
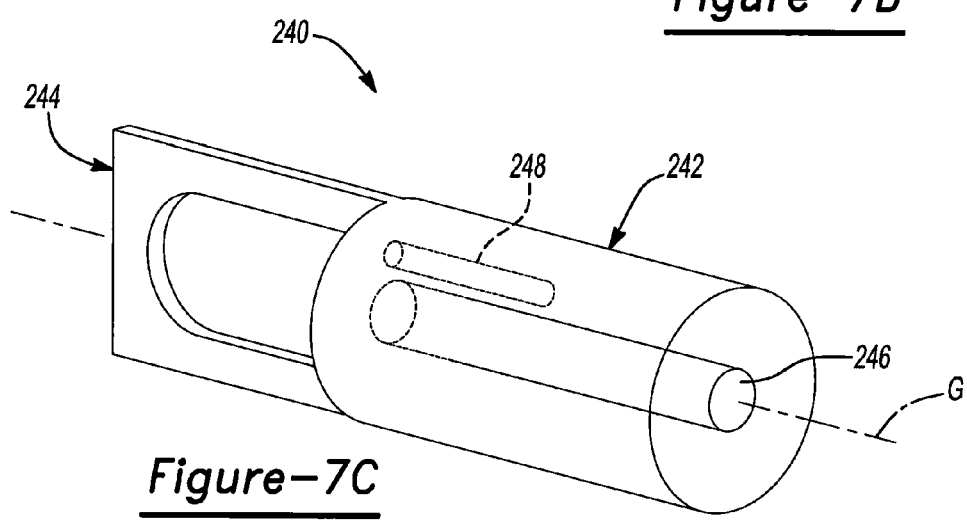

With reference to FIG. 7C, a spacer 240 is illustrated. The spacer 240 may include a body portion 242 from which extends an attachment region 244. The body portion 242 may be formed in any appropriate shape or size, but may be formed as a substantially cylindrical portion extending along an axis G. The body portion 242 may also define a central cannula 246 which extends along the length of the body portion 242 and also substantially along the axis G. The cannula or any other region may be provided for selected purposes, such as allowing for passage of a guide wire or the like.

The attachment region 244 may be affixed to the body region 242 and interconnected therewith in any appropriate manner. For example, the attachment region may be substantially rigid and be formed in generally integrally or as one piece with the body region 242. Therefore, the spacer 140 may be formed a single piece, such as with molding or casting of various materials. Moreover, the spacer 240 may be formed of any appropriate material such as a ceramic, polymer, metal, metal alloy or combinations thereof. The attachment region 244 allows for attachment of the spacer 240 to a selected member such as the anchor 20. Therefore, the anchor 20 may be interconnected with the spacer 240 for assisting in fixation of a selected soft tissue portion. In addition, the body region 242 may define external grooves or recesses 248 that may extend along a length of the body region 242. Selected portions, such as portions of an implant or a suture member, may be fitted into or engage the groove 248 for positioning the spacer 240 or for fixation of the spacer 240.

Figure 8:
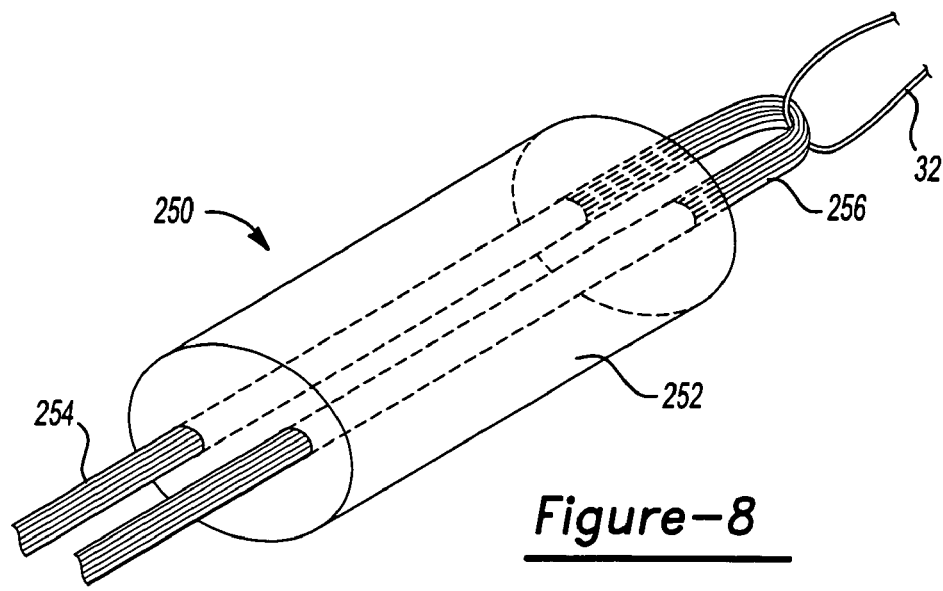
FIG. 8 is a top perspective view of an integrated spacer according to various embodiments.

With reference to FIG. 8, a spacer assembly 250 is illustrated. The spacer assembly 250 includes a block portion or body 252 that may be formed around a selected graft 254. The graft 254 may be any appropriate implant portion such as a tendon or a ligament replacement. The graft 254 portion may define a substantially unitary strand or member that may be formed in the block 252 and interconnected with the connection strand or suture 32 or any other appropriate mechanism. The graft 254 may be looped through the body 252 to form a graft loop 256 at an end of the body 252 opposite the ends of the trailing strand ends of the graft 254.

Figure 8A:
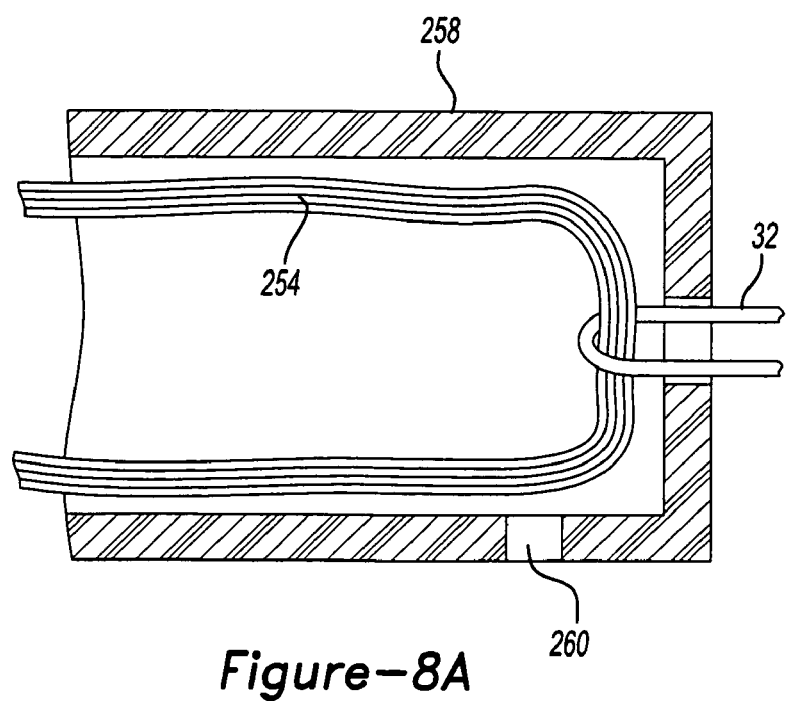
FIG. 8A is a detailed cross-sectional view of a mold to form the spacer.

Although the graft 254 may be formed into the body 252 in any appropriate manner, the graft 254 may be formed into the body 252 by molding a selected moldable material, such as polymer, that may include a bone cement or bio-absorbable polymer, or other materials such as a bone mulch and the like. With reference to FIG. 8A, the graft 254 may be positioned in a selected mold 258. The mold 258 may be formed in any appropriate manner and include an internal geometry or shape defined by a wall of the mold 258 to form the selected body 252. The mold 258 may define a port 260 that allows access to an interior of the mold 258 so that the moldable material may be passed into the interior of the mold 258 to be cured or set up. In this way, the graft 254 may be positioned in the mold and attachment suture 32 or other appropriate portion be interconnected with the graft 254.

After the graft 254 is positioned in the mold 258, the moldable material may be inlet into the mold 258 and allow to cure around the graft 254. The mold 258 may then be appropriately removed from the area to allow interconnection of the graft 254 with a selected portion such as the anchor 20. It will be understood that any appropriate material may be injected into the mold 258 or poured into the mold through any appropriate access port. Also, the mold 258 may be provided either during a procedure or may be preformed depending upon the selected procedure. In addition, the mold 258 may be substantially customized such that a selected area may be appropriately filled with the body 252. Nevertheless, the body 252 may be substantially customized or selectively formed for various procedures to allow for a substantially custom fit for assuring an appropriate positioning of the spacer body 252.

An exemplary method of performing a procedure using the anchor 20 and the spacer 220 is illustrated. It will be understood that although the anchor 20 and the spacer 220 are described as an exemplary way of performing a method of using an anchor or spacer, it will be understood that any appropriate anchor or spacer may be used. In addition, the anchor 20, or any appropriate anchor, may be used alone and not with the spacer 220, or any appropriate spacer. Likewise, the spacer 220, or any appropriate spacer, may be used with any appropriate portion and not with the anchor 20 or any other appropriate anchor. Therefore, it will be understood that the following method described and illustrated as merely exemplary of a method of performing a selected procedure and is not intended to limit the procedure.

Figure 9:
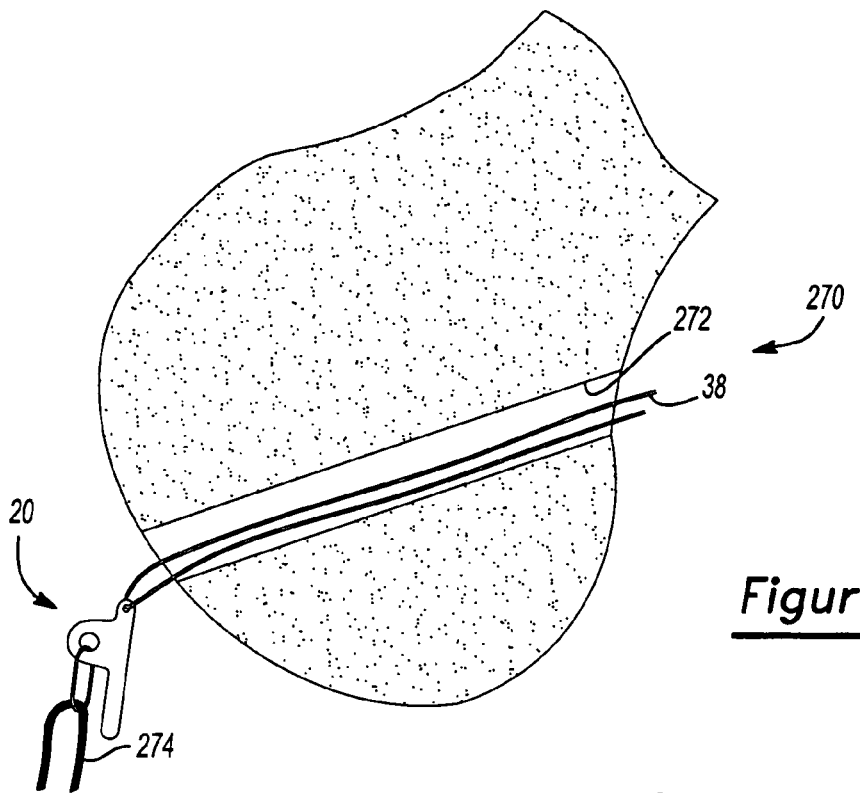
FIG. 9 is an cross-sectional view of a femur exemplary illustrating a soft tissue anchor according to various embodiments in an unimplanted position.

With initial reference to FIG. 9, a procedure may be performed relative to a femur 270 of an anatomy. For example, a bore 272, also known as femoral bore 272, may be formed through a portion of the femur. Although the following description relates generally to the replacement of an anterior curiciate ligament (ACL), it will be understood that the various methods and the instruments may be used for any appropriate procedure in an ACL replacement or reconstruction is merely exemplary. In addition, it will be understood that the ACL graft is generally interconnected with the tibial portion, not particularly illustrated, but generally known in the art. Likewise, the femoral bore 272 may be formed using any appropriate instruments, such as drill or reamer. These are generally known in the art and not described in detail herein.

Nevertheless, once the bore 272 is formed, or at any other time appropriate to the procedure, the anchor 20 may be positioned to be moved through the bore 272. The anchor 20 interconnected with the activation suture 38 may also be interconnected with a graft portion 274. The graft portion 274 may be any appropriate graft portion, such as an allograft or zenograft, that may either be natural or synthetic materials. In addition, the attachment suture 32 is generally provided through the eyelet 30 of the anchor 20. The suture 32 may include a plurality of loops that may be formed from a single strand or a plurality of strands. Nevertheless, the attachment suture 32 may include a plurality of strands of a suture material for various reasons, such as reduced creep and stretching of the suture to further insure appropriate positioning of the graft 274. The graft 274 may be interconnected with the anchor 20 in any appropriate manner. For example, the graft 274 may also be passed simply through the eyelet 30 rather than being interconnected with the attachment suture 32. The graft 274 may be interconnected with the anchor 20 prior to a procedure or inneroperatively. Similarly, the activation suture 38 may be interconnected with the anchor 20 at any appropriate time.

Nevertheless, once the bore 272 is formed through the femur 270, the activation suture may be passed through the bore 272. The activation suture 38 may be passed through the bore 272 in any appropriate manner. For example, a guide wire may be used to assist in forming the bore 272 which may be interconnected with a end of the activation suture 38 to assist in passing the activation suture 38 through the bore 272 of the femur 270. Once the activation suture 38 is passed through the bore 272, the activation suture 38 may be used to assist in passing the anchor 20 through the femoral bore 272.

The activation suture 38 is interconnected with the activation portion 24 of the activation lever 26 of the anchor 20. Therefore, manipulating the activation suture 38 may assist in moving the anchor 20 through the femoral bore 272. The activation suture 38 may be used to urge the anchor 20 into any appropriate position in the femoral bore 272 or through the femoral bore 20.

Figure 10:
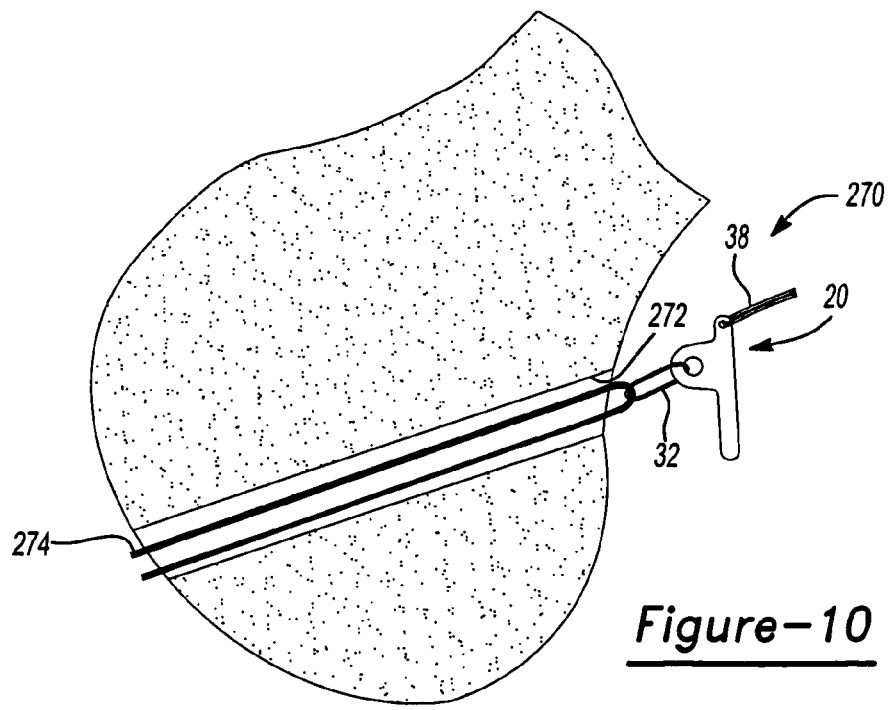
FIG. 10 is a cross-sectional view of a femur exemplary illustrating the soft tissue anchor according to various embodiments in an partially implanted orientation.

With reference to FIG. 10, the anchor 20 may be passed through a substantial portion of the femoral bore 272. The anchor 20 may be passed any appropriate distance through the femoral bore 272, such as a distance great enough to allow the activation lever 26 to be operated. For example, the anchor 20 may be passed a distance through the femoral bore 272 such that a majority of the activation lever 26 is free of the bore 272.

Once the activation lever 26 can be activated, the activation suture 38 may be used to activate the activation lever 26. In activating the activation lever 26, the activation lever 26 is operably moved to an activated position by rotating it a selected distance relative to the femur 270. Shown particularly in phantom in FIG. 10, the activation lever 26 may be moved a distance such that a portion of it extends beyond the edges of the bore 272. This allows the activation lever 26 to engage a selected portion of the femur 270 after the activation lever 26 has been activated.

Figure 11:
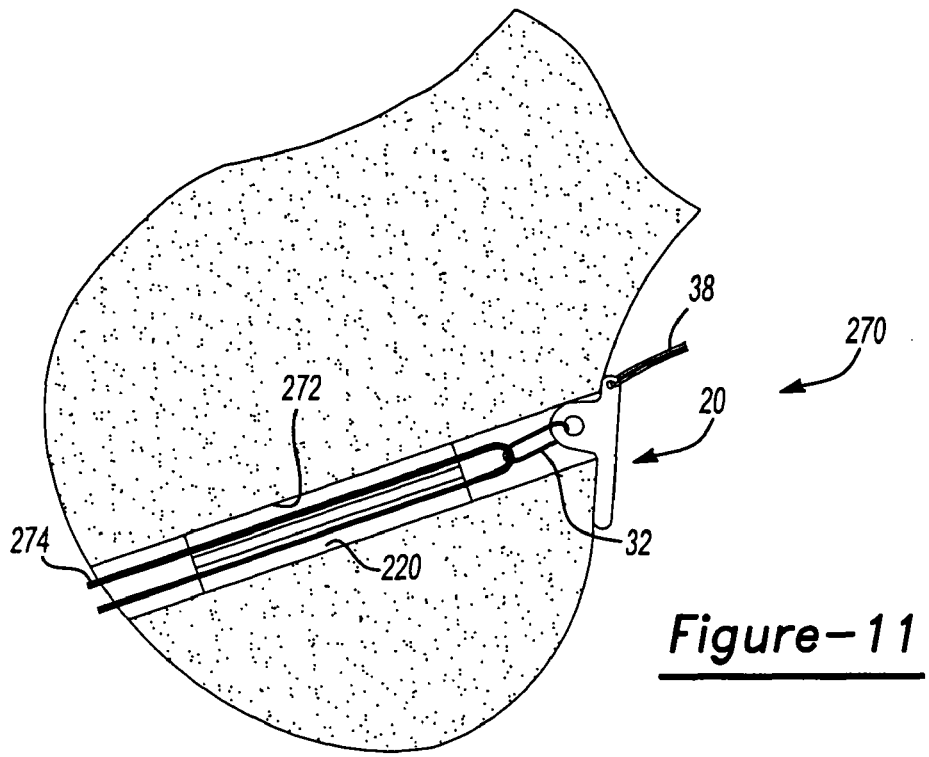
FIG. 11 is a soft tissue anchor according to various embodiments in a substantially implanted position including a spacer.

With reference to FIGS. 10 and 11, once the activation lever 26 has been activated, the graft 274 may be used to set the anchor 20 in position. The anchor 20 may be pulled adjacent to a portion of the femur 270 such that the activation lever 26 is operable to engage a surface 280 of the femur 270. In this way, the activation lever 26 engages the femur 270 such as the anchor 20 is not able to substantially move a distance through the bore 272 after the activation lever 26 has engaged the surface 280 of the femur 270. In this way, the graft 274 may be held within the bore 272 at a selected position due to the interconnection with the anchor 20. The activation lever 26 engages the femur 270 to reduce or substantially eliminate the possibility of the anchor 20 moving back through the femoral tunnel 272.

According to various embodiments, such as the anchor 20 and the spacer 220 illustrated at FIG. 7A, may also engage the graft 274 that is positioned in the femoral tunnel 272. The spacer 220 interconnects with the connection suture 32 through the connection 22. The graft 274 may be looped through the connection suture 32 and over the spacer 220. The spacer 220 may fill a portion of the bore 272 such that the graft 274 may not be allowed to substantially bind on the connection suture 32. For example, the spacer 220 forces apart or holds apart the portions of the graft 274 such that the pressure on the graft 274 may be spread over a greater area rather than at a very small area next to the connection suture 32.

In addition, the spacer 220 may assist in positioning the graft 274 near the wall of the femoral tunnel 272. This may assist in ingrowth of natural tissue into the graft 274 to assist in fixation of the graft 274 in the femoral tunnel 272. In addition, the spacer 220 may be sized to substantially engage a portion of the femoral tunnel 272 such that the bone may grow into the spacer 220. In this way, the spacer 220 may also assist in fixing the graft 274 to a selected position in the femoral tunnel 272. In addition, the spacer 220 may be interconnected with the anchor 20, or any appropriate anchor or assembly according to various embodiments, to at least initially hold the graft 274 at a selected position.

Therefore, it will be understood that any appropriate spacer, such as the spacer 220 may be used with any appropriate anchor, such as the anchor 20, to assist in connecting the graft 274 in the femoral tunnel 272. In addition, the spacer 220 may assist in allowing a long term interconnection of the graft 274 with the femoral tunnel 272 while the anchor 20 may provide the substantially initial and temporary fixation of the graft 274 relative to the femoral tunnel 272. Alternatively, all portions of the connection may be substantially permanent such that the graft 274 may be mechanically fixed relative to the femoral bore 272.

It will be understood that the anchor may pass through a portion of a bore, such as the femoral bore 172, to allow for holding a selected soft tissue, such as an ACL graft 174, relative to a selected portion. Although the ACL graft 174 may be fixed relative to the femoral bore 172, it will be understood that any appropriate soft tissue portion may be fixed or held relative to a selected portion with an appropriate anchor. Simply providing the ACL graft is exemplary of various procedures and implants.

Figure 12:
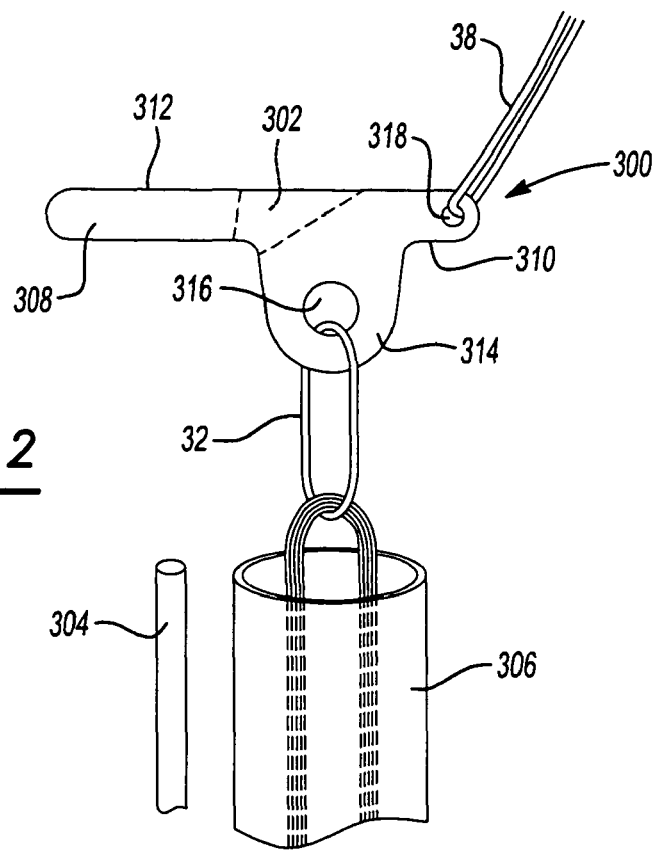
FIG. 12 is a plan view of an assortment of portions to assist in positioning the anchor according to various embodiments.

Positioning the anchor 20, or any appropriate anchor, can be performed in a plurality of ways, such as rotating the anchor 20 with the flexible strand 38 or other appropriate mechanisms for performing a selected procedure. For example, with reference to FIG. 12, an anchor 300, similar to the anchor 20, may include a channel or opening 302 that may act as a passage for a member, as discussed herein, formed therein. The opening 302 may be formed in any appropriate portion of the anchor 300 to interact with a selected member, such as a resiliently flexible rod or positioning member 304. The entire assembly, as discussed herein, including the rod 304 and the anchor 300 may be positioned through a selected member, such as a tube 306 for positioning the anchor 300 relative to the a portion of the anatomy.

The anchor 300 may be similar to the anchor 20, as illustrated in FIG. 1A. Therefore, the anchor 300 may include a first flange 308 similar to the first flange 22 and a second flange 310 similar to the second flange 24. The first and second flange 308, 310 generally define a lever arm or portion 312 of the anchor 300 that may be manipulated as described herein. Extending from the lever arm 312 is a holding or engaging portion 314, similar to the holding or engaging portion 28 described above. The engaging portion 314 generally defines a fixation portion or bore 316. Positioned through the fixation bore 316 may be a suture or strand 32. Alternatively, as discussed above, a selected soft tissue portion, such as a tendon graft, may be positioned directly through the fixation bore 316. Further, the second flange 310 may define a passageway 318 and may interconnect with a suture or strand portion 38.

Although the anchor 300 may be similar to the anchor 20 described above, the anchor 300, according to various embodiments, it may also include the channel 302. The channel 302 may be any appropriate channel and formed in any appropriate manner in the anchor 300. For example, the anchor 300 may be formed of a polymer or moldable material such that the channel 302 is molded into the anchor 300 during formation of the anchor 300. Alternatively, or in addition thereto, the channel 302 may also be machined or finished to form the channel 302 in the anchor 300.

Regardless of the method of forming the channel 302, the channel 302 may interact with the resiliently flexible member 304 to assist in positioning the anchor 300 in a selected position. The flexibly resilient member 304 may be any appropriate member, such as a K-wire™ or formed of a shape memory material such as nitinol. Regardless, the resiliently flexible member 304 may be positioned relative to the channel 302 to position the anchor 300 in a selected position relative to the tube 306 for positioning the anchor 300 in the selected orientation. The anchor 300 may be provided as a kit, including the resiliently flexible member 304 and the tube 306 and other appropriate portions. For example, the anchor 300 may be provided with the anchor 20, the anchor 152, or any appropriate anchor. Further, the tube 306 may be similar to the tube 130 described above. Further, the anchor 300 may be provided with a selected spacer portion, such as the spacer 184, 198, or any appropriate spacer. Therefore, it will be understood that the anchor 300 may be included in any appropriate embodiment and it is described with the resiliently flexible member 304 and the tube 306 for illustration only.

The anchor 300 may be used for any appropriate procedure, such as an ACL replacement. Although the anchor 300 may be used to replace any appropriate soft portion or for fixing a selected soft tissue portion or graft relative to another portion of the anatomy, the discussion herein relates to the replacement of a natural or anatomical ACL with a graft. It will be understood that the method described in relation to FIGS. 13 and 14 is merely exemplary and not intended to limit the teachings herein.

Figure 13:
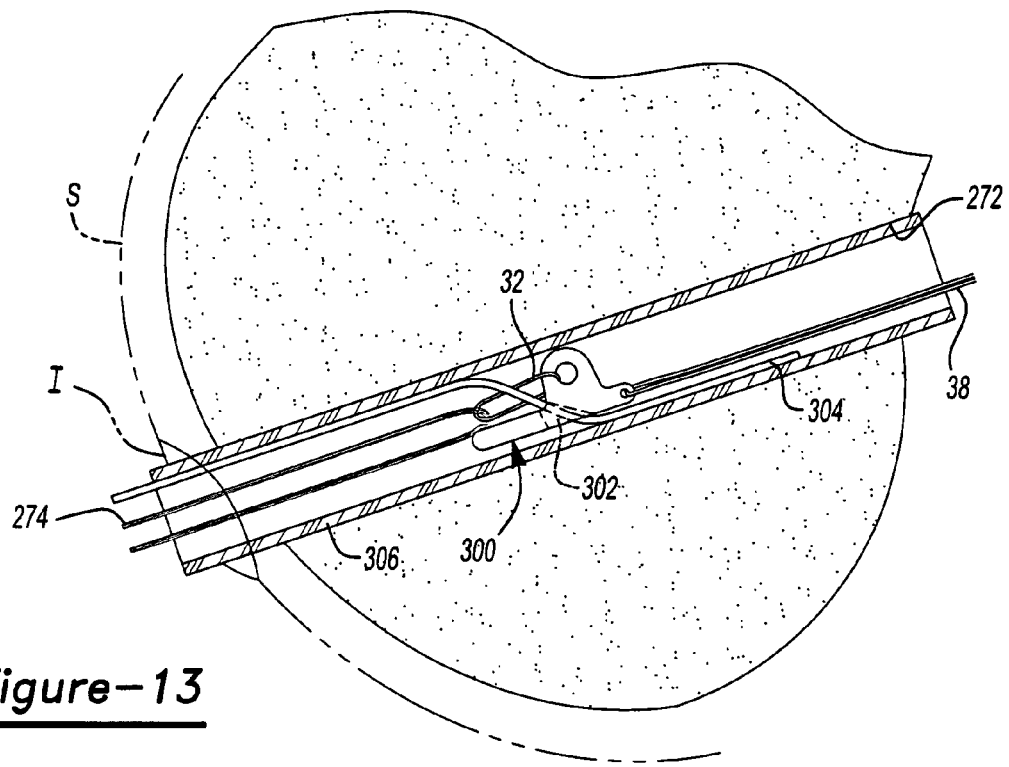
FIG. 13 is a detail cross-sectional view of a portion of an anatomy including the anchor in a partially implanted position.
Figure 14:
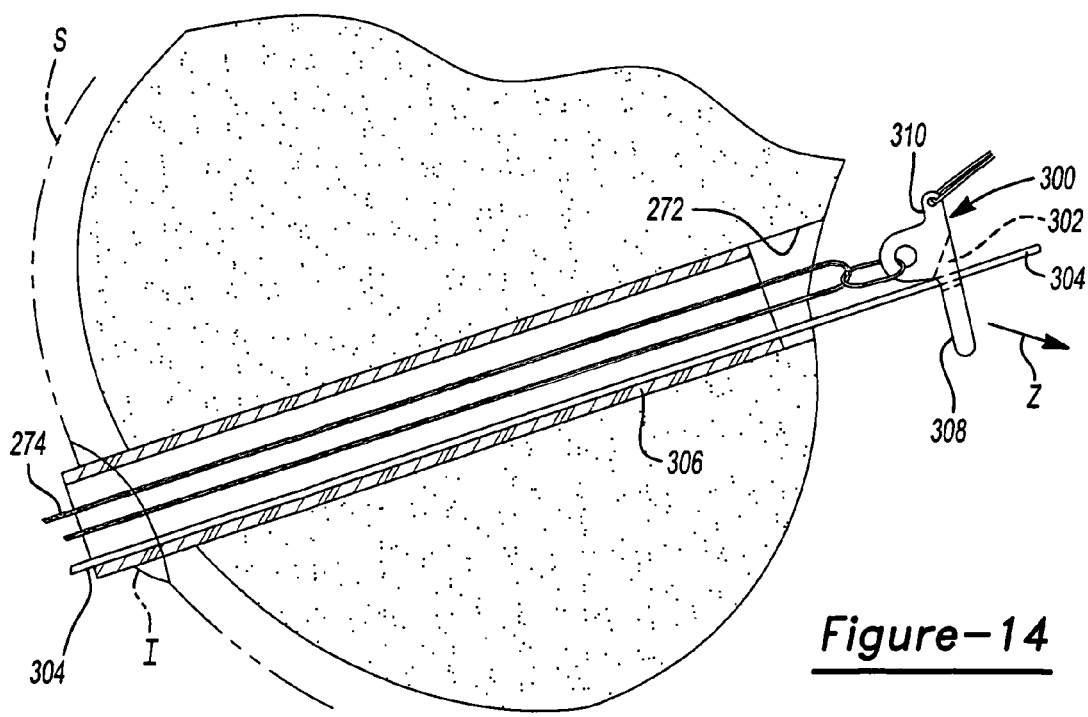
FIG. 14 is a detail cross-sectional view of a portion of an anatomy including the anchor in a partially deployed position.

With initial reference to FIG. 13, the femur 270 may be prepared by forming an incision I through soft tissue including the skin and other soft tissues, such as the determis, muscle and the like. The incision I may allow access for various instruments, such as a drill, to be positioned relative to the femur to form the tunnel 272 in the femur. The tunnel 272, as described above, can be used to house the graft 274 after implantation. Further, as described above, the tunnel 272 may allow for direct contact with the graft 274 to allow for a natural fixation or bone ingrowth into the graft 274 after positioning in the tunnel 272.

Once the tunnel 272 is formed in the femur 270, the anchor assembly including the anchor 300, the resiliently flexible member 304 and the tube 306 may be positioned through the tunnel 272. It will be understood that for various procedures, such as an ACL replacement, that the tunnel 272 may be substantially co-axial with a tunnel formed in a tibia and the tube 306 may be also passed through the tibia. Regardless, discussion relative to the femur is merely illustrative regardless a method of use of the anchor 300 according to various embodiments.

The anchor assembly may be passed through the tunnel 272 by pushing the tube 306 through the tunnel 272 and/or also drawing on the placement member 308. Further, the resiliently flexible member 304, being positioned through the channel 302, may also be used to move the anchor 300 relative to the tunnel 272 and within the tube 306. After being passed through the channel 302 and positioned in the tube 306, the flexible member 304 may be flexed relative to the anchor 300. Further, the flexible member 304 may compress the anchor 300 relative a selected portion of the tube 300 to assist in positioning the anchor 300 relative to the tube 306. Further, as illustrated in FIG. 13, when the anchor is in the unactivated or undeployed orientation, such as within the tube 306, the flexible member 304 is substantially flexed. Regardless, the member 32 may be positioned through the anchor 300 and interconnected with the graft 274 to position the graft 274 relative to the tunnel 272.

With reference to FIG. 14, once the assembly is passed a selected distance through the femur, the anchor 300 may be moved to a position exterior to the tunnel 272. Once the anchor 300 is exterior to the tunnel 272, the tube 306 may be withdrawn into the tunnel 272. Once the tube 306 is withdrawn into the tunnel 272, the flexible member 304 may decompress and retain or regain its non-compressed orientation. Once the anchor 300 that was positioned in the tube 306 is passed through the tunnel 272, the tube 306 is withdrawn into the tunnel 272 to allow the anchor 300 to move to the deployed position. Though as discussed herein, the tube 306 may not be necessary and the anchor 300 may be positioned in the tunnel 272 with the flexible member 304 for positioning the anchor 300.

The anchor 300 may move in the direction of arrow Z. The anchor 300 moves generally in the direction of arrow Z due to the decompression of the flexible member 304. Moving the tube 306 from a position that no longer surrounds the anchor 300, allows the flexible member 304 to decompress and orient or move the anchor 300 due to its position in the channel 302 of the anchor 300. The movement of the anchor 300 allows the first flange 308 to be moved to a position that allows it to engage a portion of the femur 270 beyond the edge of the tunnel 272 and the second flange 310 to move to engage a second portion of the femur beyond the tunnel 272. As discussed above in relation to the anchor 20, the flanges allow for holding the anchor 300 relative to a selected position, such as at the end of the tunnel 272, to hold the graft 274 in a selected position. The flexible member 304, as it decompresses, assists in moving the anchor 300 to its selected deployed position. This may help ensure that the anchor 300 is moved to the selected deployed position and can be positioned against the bone. Particularly when the anchor 300 is being positioned in a substantially closed or minimally invasive procedure, such as with an arthroscope or other minimally invasive procedures, the flexible member 304 may assist in positioning the anchor 300 in the deployed position.

Accordingly to various embodiments, the tube 306 may not be used in the anchor assembly. The anchor 300 may be positioned relative to the tunnel 272 with the flexible member 304. As illustrated in FIG. 13, the flexible member 304 may be positioned in a compressed position when the anchor 300 is in the non-deployed position. Rather than providing the tube 306, however, the dimension of the tunnel 272 may be provided to position the anchor 300 in the undeployed position and form the compression of the flexible member 304. Therefore, once the anchor 300 is moved to a position outside of the tunnel 272, such as by pushing the flexible member 304 or pulling on the flexible member 38, the anchor 300 may move to the deployed position. Similar to the deployed movement in FIG. 14, the anchor 300 may move generally in the direction of arrow Z assisted at least in part by the decompression of the flexible member 304. Although the tube 306 may be withdrawn into the tunnel 272 to allow for deployment of the anchor 300 as illustrated in FIG. 14, moving the anchor 300 from the tunnel 272 may provide a release of the compression of the flexible member 304 and to allow deployment of the anchor regardless of the position or use of the tube 306. Therefore, it will be understood that the implantation and positioning of the anchor 300 may be performed according to various methods, such as with the tube 306, without the tube 306, or using the tube 306 for a portion of the procedure.

Regardless, using the flexible member 304 may allow for ensuring that the anchor 300 has been positioned in the deployed position. Because the flexible member 304 can be provided to return to the non-compressed position once the anchor 300 has been removed from the tube 306 or from the tunnel 272, it can be substantially assured that the anchor 300 is moved into the deployed position before tightening the graft 274 according to various embodiments. Further, including the flexible member 304 may also provide for confirmation of movement of the anchor 300 into the deployed position. After positioning the anchor 300, the graft 274 may then be properly tensioned and the strand 38 may be used to assist in holding the anchor 300 in its selected position relative to the tunnel 272. Therefore, providing the tube 306 with, either alone or in combination, the flexible member 304, may assist in implanting or positioning the anchor 300 and ensuring its proper deployment.

As discussed above, a material, such as a tissue graft, can be positioned in an anatomical portion according to various embodiments. Additionally, an anchor member can be positioned relative to a selected portion of the anatomy, such as the femur 270 while a flexible member is drawn through a selected portion of the femur 270 to be interconnected with the graft member.

With reference to FIG. 15, an anchor member 350 is illustrated. The anchor 350 can include a body portion 352 that can be formed in any appropriate shape. The body portion 352 can be substantially cylindrical, oval in cross section, polygonal in cross section or any other appropriate shape. Extending from the body 352 can be a catch portion or cross member 354 that can act as a collar and extend a distance from the body 352 to define a ledge 356. The ledge 356 can be used to engage a selected portion of the anatomy, as discussed further herein. Also, the cross section of the collar 354 can be any appropriate cross section such as substantially oval, circular, polygonal, or the like.

The anchor member 350 can further define an internal passage 358. The internal passage 358 can be formed in any appropriate manner with the anchor member 350. For example, the internal passage can be molded, milled, or otherwise formed. The anchor member 350 can be formed of any appropriate material such as a polymer, a metal, metal alloy, a natural material (i.e. one harvested from an anatomical source) or any appropriate material. Nevertheless, the passage 358 can be formed to include a plurality of diameters such as a first diameter 360 and a second diameter 362. The second diameter can be defined by a projection or internal collar 364 defined within the passage 358. The collar 364 can be used to support a selected portion of the anchor assembly 350, as discussed further herein.

A flexible member 370 can be provided to pass through the passage 358. The flexible member 370 can be any appropriate flexible member such as a wire, a suture, a graft material, etc. The flexible member 370 can be knotted in a slip knot 372 such as those generally known in the art. The slip knot 372 can divide the flexible member 370 into a graft engaging or selectable (non-fixed) portion 374 and a manipulating or activation portion 376. The graft engaging portion 374 can be used to engage or allow a graft to be placed through a loop formed by the graft engaging portion 374. The graft engaging portion can be a selectable portion that allows the graft engaging portion to be selectively sized relative to the anchor member 350. The manipulating portion 376 can be used to manipulate the entire flexible member 370, as discussed further herein.

The slip knot 372 can rest upon the collar 364 to resist movement of the flexible member 370 generally towards a first end 351 of the anchor assembly 350. Nevertheless, the manipulating portion 376 can be used to decrease the size of the graft engaging loop 374 to assist in positioning the anchor assembly 350 relative to a selected portion of the anatomy, as discussed further herein.

It will be understood that any appropriate configuration of the anchor assembly 350 can be provided. With reference to FIG. 15B, an anchor assembly 350' is illustrated. The anchor assembly 350' can be substantially similar to the anchor assembly 350 and include a body portion having a first end 351' and an internal passage 358'. The internal passage 358', however, can define a collar 380 that includes a first passage 382 and a second passage 384. The passages 382, 384 can allow the flexible member 370 to pass therethrough. A graft engaging loop 374 can still be defined while a manipulating portion 376 can also be defined. Nevertheless, the slip knot 372 need not be provided as the collar 380 can be provided to assist in moving the flexible member 370 relative to the anchor body 350 and further manipulate a graft, as discussed further herein. The manipulating portion 376 can then be locked relative to the collar 380, such as with a fixed not or locking member.

Figure 15A:
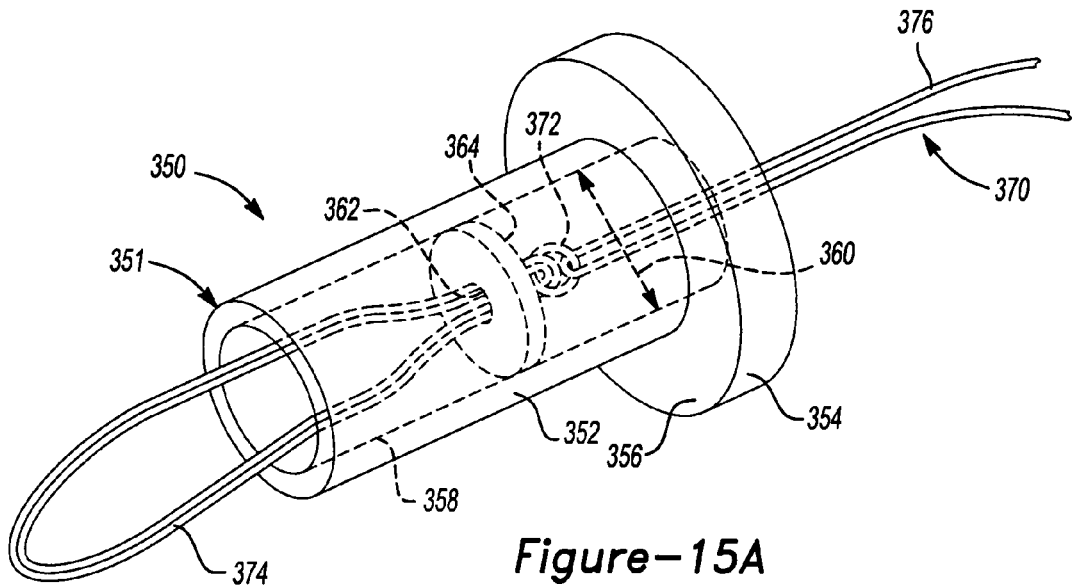
FIG. 15A is a perspective view of an anchor assembly according to various embodiments.
Figure 15B:
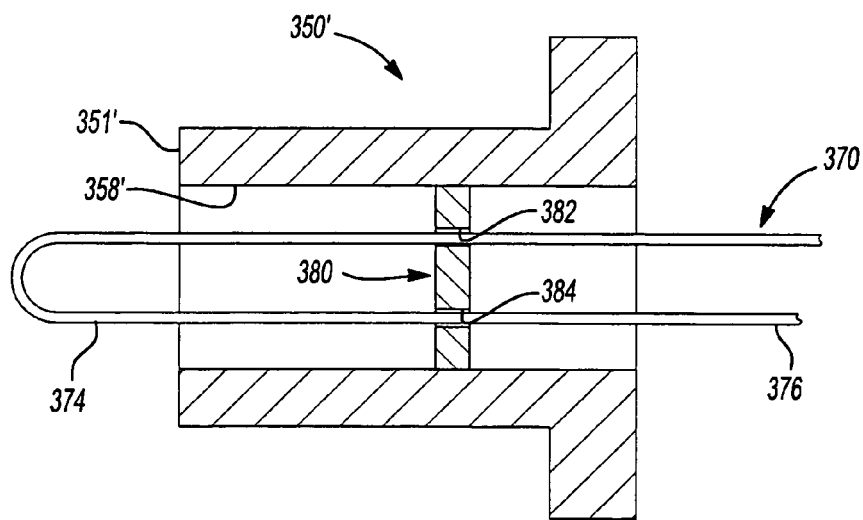
FIG. 15B is a cross-section view of an anchor assembly according to various embodiments.

In addition to the anchor members illustrated in FIGS. 15A and 15B, the flexible member 370 can also be provided as an adjustable suture loop or an adjustable loop. Various adjustable loops are described in U.S. patent applications Ser. No. 11/541,505 entitled "Method And Apparatus For Forming A Self Locking Suture Loop" to Kevin Stone, and U.S. patent application Ser. No. 11/541,506 entitled "Method And Apparatus For Graft Fixation" to Kevin Stone, both filed concurrently herewith and incorporated herein by reference. The adjustable suture loops therein can be interconnected with the anchor member 350, 350' such that an adjustable portion of the adjustable suture loop is allowed to engage a graft while a manipulating portion 376, can extend through the bone, such as the femur 270, to be manipulated. The manipulating portion can manipulate the member 370 to allow for adjustment of the graft engaging portion to select a position of the graft relative to the anchor member 350, 350'. It will be understood, therefore, that any appropriate adjustable member can be used, such as any appropriate adjustable flexible member.

Figure 16:
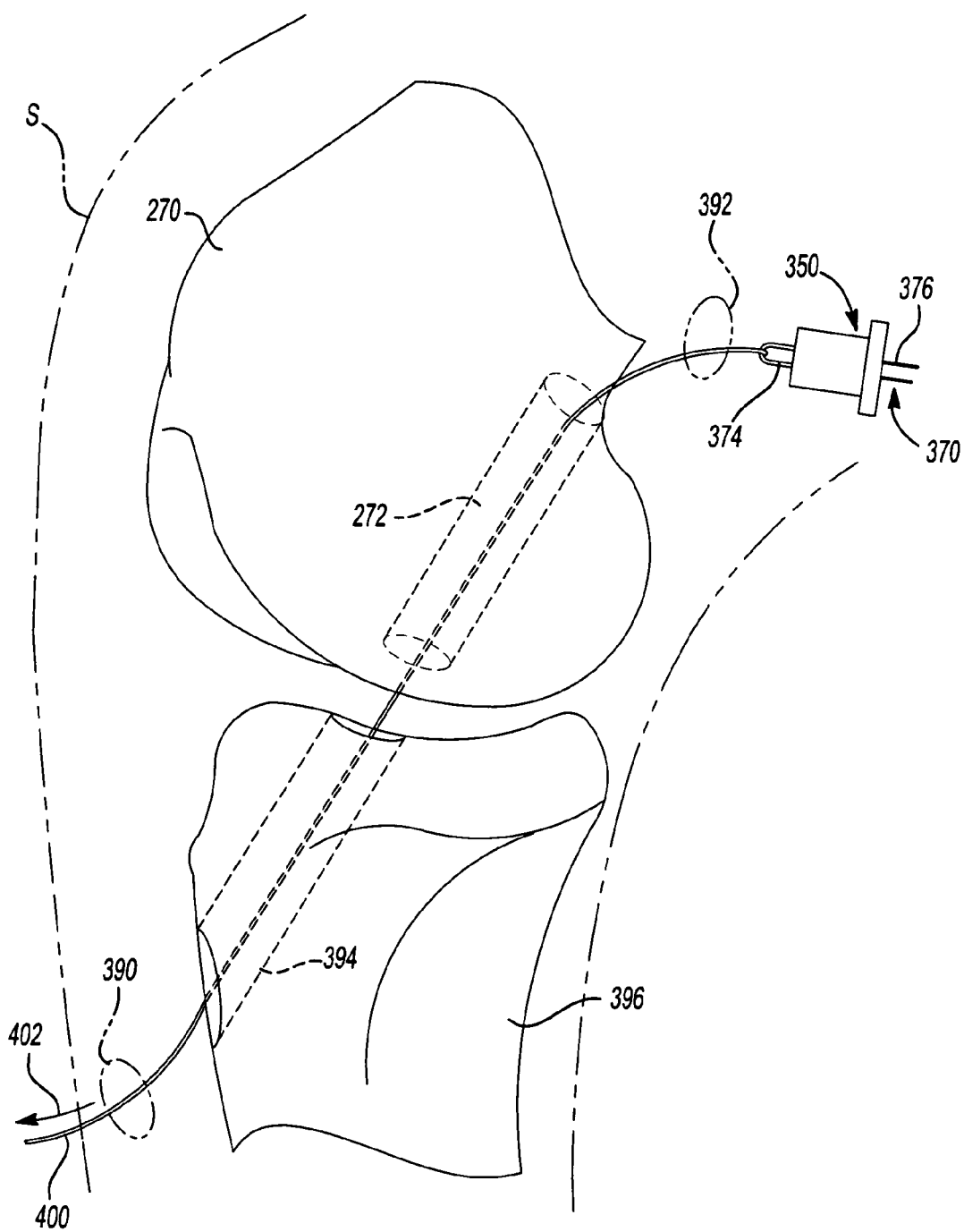
FIGS. 16-18 are environmental views of a use of an anchor assembly according to various embodiments.
Figure 18:
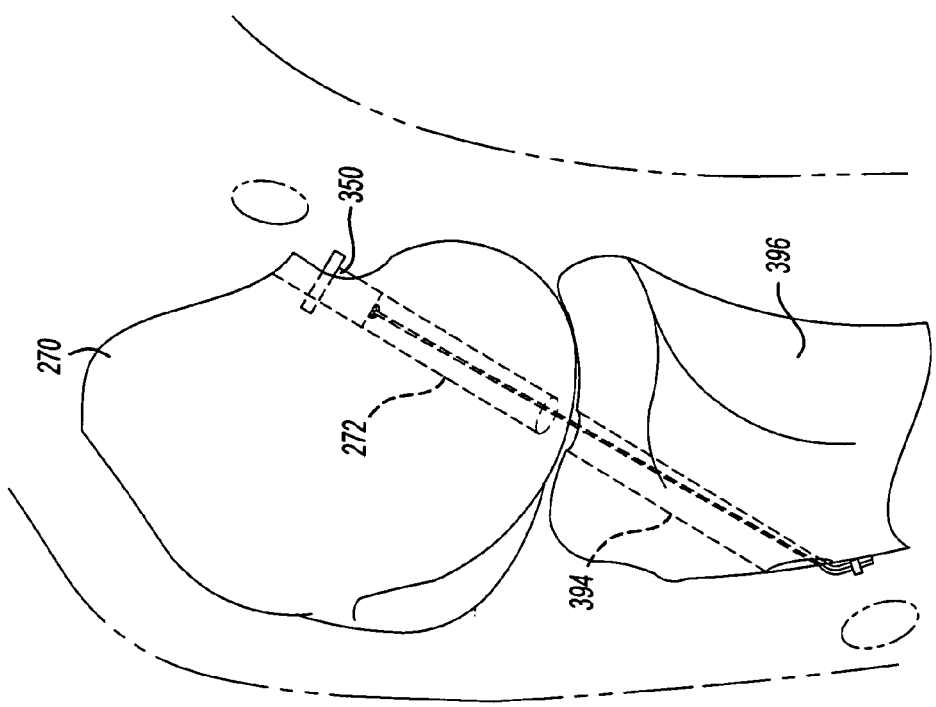
Figure 17:
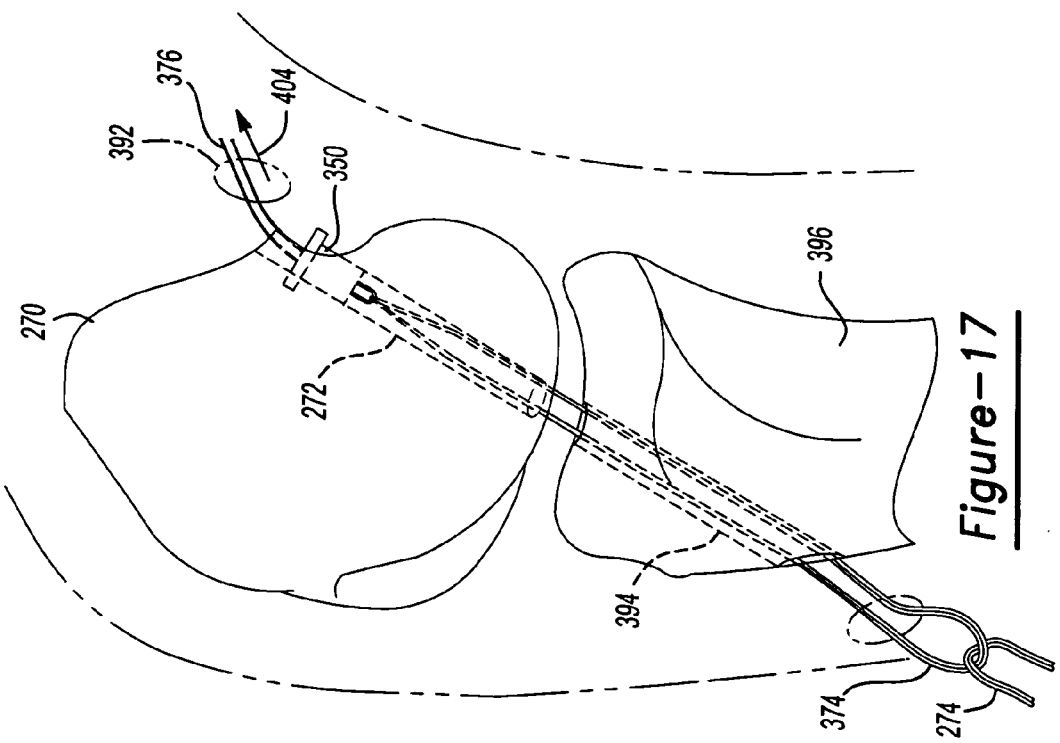

Although an anchor assembly 350, 350' according to various embodiments has been discussed, an exemplary method of using the assembly is illustrated in FIGS. 16-18. The method illustrated in FIGS. 16-18, and discussed herein, is merely exemplary and not intended to provide a limiting explanation of a use of the anchor assembly according to various embodiments, such as the anchor assemblies 350, 350'.

With initial reference to FIG. 16, a first incision 390 can be formed in the skin S. Also a second incision 392 can be formed in the skin S. The first incision 390 can be formed on an anterior side of the anatomy, such as a knee 394, while the second incision 392 can be formed on a posterior side of the knee 394. It will be understood, however, that the incisions 390, 392, can be formed relative to any appropriate portions of the anatomy and in any appropriate size.

Through the incisions 390, 392 a first tunnel 394 can be formed in a tibia 396 and the tunnel 272 can be formed as a second tunnel in the femur 270. The tunnels 394, 272 can be formed in any appropriate manner, such as those generally known in the art, and will not be described in detail herein. The tunnels 394, 272 are generally aligned though the tibia and the femur during formation of the tunnels. Also, the tunnels 364, 372 can be of any appropriate diameter or multiple diameters along the length of either or both of the tunnels 391, 372. It will be understood that a portion of the assembly, such as the flexible member 370 can pass through the tunnel while the anchor member 350, 350' may not.

Once the tunnels 394, 272 are formed, a grasping member 400 can be passed through the tunnels 394, 272 to engage the graft engaging loop 374. The grasping member 400 can be any appropriate tool such as a K-wire, a wire grasper, or the like. Further, it will be understood that the grasping member 400 can also be a guide wire that can be inserted through the tibia 396 and the femur 270 to assist in guiding the formation of the tunnels 394, 272 such that the grasping member 400 is actually provided in the tunnels during their formation and not inserted therethrough after their formation. Nevertheless, the grasping member 400 can be pulled generally in the direction of arrow 402 to pull the graft engaging loop 374 through the tunnels 272, 394 and possibly through the incision 390 if selected.

With reference to FIG. 17, once the graft engaging loop 374 has been drawn through the tunnels 394, 272 the graft 274 can be looped over the graft engaging loop 374. The anchor body 350 can be engaged in the tunnel 272 formed in the femur 270 and the actuation portion of the flexible member can be pulled generally in the direction of arrow 404 to draw the graft engaging loop 374 and the graft 274 through the tunnels 394, 272. It will be understood that the actuation portion 376 of the flexible member 370 can be actuated and, due to the slip knot 372, the collar 380, or any appropriate mechanism, allows for drawing the graft engaging loop 374 through the tunnels 394, 372. Because the graft 274 is engaged on the loop 374 the graft 274 can be moved through the tunnels 394, 272. Also, the edge 356 can assist in holding the anchor member 350 relative to the femur 270 while the actuation portion 276 is being pulled.

With reference to FIG. 18, once the soft tissue graft 274 is positioned in the tunnels 394, 272 in an appropriate manner, the anchor assembly 350 can be appropriately seated or finally seated in the tunnel 272 of the femur 270. The seating of the anchor assembly 350 can be assisted by tensioning the soft tissue graft 274 in the tunnels 394, 272. The tensioning of the graft 274 can be performed in any appropriate manner, such as those generally known in the art. Nevertheless, the tensioning of the graft 274 assists in seating the anchor member 350 relative to the femur 270. Further, the end of the soft tissue graft near the tibia 396 can be fixed relative to the tibia 396 in any appropriate manner. For example, the Washer-Loc® provided by Arthrotek, Inc. of Warsaw, Ind. is one appropriate mechanism to fix the end of the graft 274 relative to the tibia 396. It will be understood, however, that any other appropriate mechanism may be provided to fix the soft tissue graft 274 relative to the tibia 396 after tensioning soft tissue graft 274. Also, the graft 274 can be any appropriate graft, such as those discussed above and including both natural or synthetic materials that can be allograft, xenografts, and autografts, or combinations of these.

Figure 19:
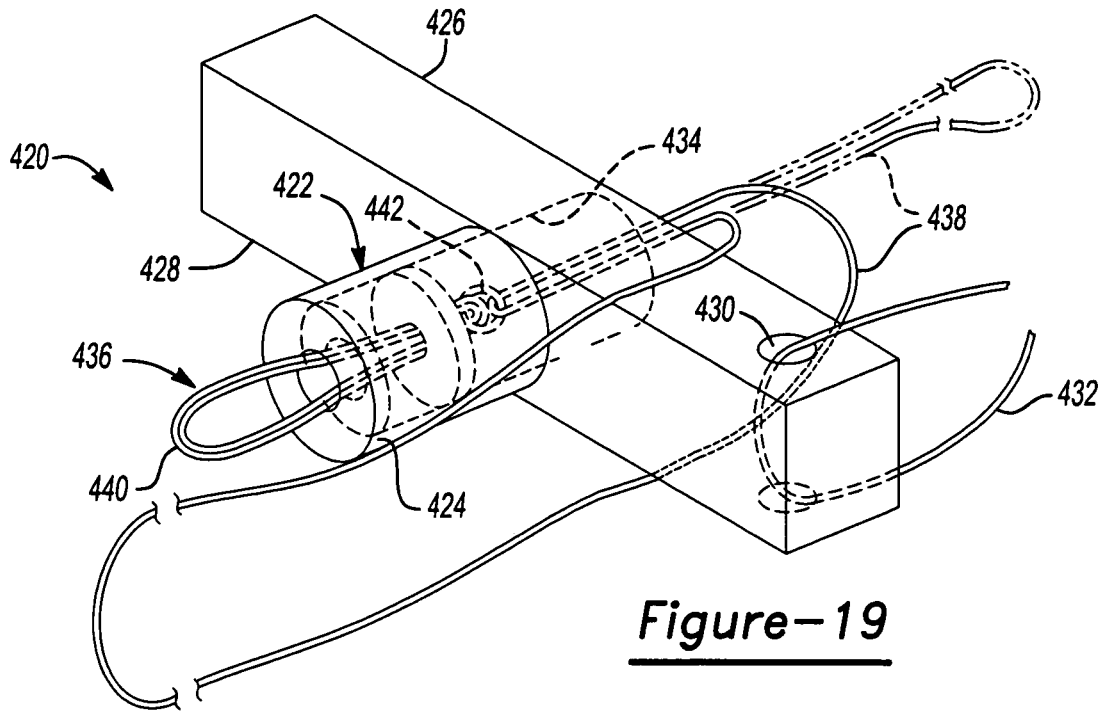
FIG. 19 is a perspective view of an anchor assembly according to various embodiments.

Various embodiments for anchoring a selected member relative to the anatomy can include an anchor assembly 420 illustrated in FIG. 19. It will be understood that the anchor assembly 420 can be used in any appropriate manner, according to various embodiments. It will also be understood, that anchor assemblies according to various embodiments described throughout can also include various other features in any appropriate combination, such as those discussed further herein.

With reference to FIG. 19, the anchor assembly 420 can include an anchor member body 422 that includes a main body portion 424 and a cross member or holding member 426. The cross member 426 can extend a distance from the main body 424 to define a ledge or edge 428. The edge 428 can engage a selected portion of the anatomy, such as the femur 270 discussed further herein.

The cross member 426 can define a guide or movement for 430. The guide bore 430 can be engaged with a flexible member or appropriate guiding member 432. As discussed herein, the guiding member 432 can assist in moving the anchor assembly 420 in a selected portion of the anatomy. The main body 424 and a portion of the cross member 426 can define a bore or passage 434. The bore 434 can be similar to the bore 358 defined in the anchor assembly 350 discussed above. The bore 434 can allow a flexible member or capturing member 436 to pass through the bore 434 through the anchor assembly 420. The cross member 426 can define a surface or portion to engage a bore, as discussed herein.

The flexible member 436 can include an actuation end 438, a graft engaging end 440 and a slip knot or actuation coupling 442. The flexible member 456 can be similar to the flexible member 370 discussed above. Therefore, similar to the anchor members according to various embodiments, the flexible member 456 can be used in combination with the anchor body 422 to hold a selected portion relative to a portion of the anatomy as discussed herein. The slip knot 422 can be provided according to any appropriate embodiment, such as those generally known in the art or an adjustable suture loop as discussed above, that allows for movement of the actuation end 438 to move the graft engaging end 440. For example, as discussed in relation to the anchor assembly 350, the actuation member 438 can be used to manipulate the flexible member 436 to achieve a selected result.

The actuation end 438, as discussed further herein, can be provided to extend through either of the tunnels formed in the bone, including the tunnel 394 in the tibia 392 or the tunnel 272 in the femur 270. This can allow the actuation end 438 to be actuated by a user from either side of the joint, such as the knee, or wherever is most appropriate for ease of use of the user. Therefore, the actuation member 438 can be held while the anchor member 420 is moved through the tunnels 394, 272, or can be pulled through the tunnel with the anchor member 420. Nevertheless, it will be understood that the actuation end 438 can be used by the user to actuate or move the graft engagement portion 440 in any appropriate manner.

The anchor assembly 480, including the body 422 can be formed of any appropriate material. For example, various polymers, metals, metal alloys, or similar materials can be used to form the anchor body 422. The anchor body 422 can be generally biocompatible and also bioabsorbable or resorbable if selected. Nevertheless, the anchor body 422 can be operable to anchor a selected portion or member relative to a portion of the anatomy. Further, the anchor body 422 can be dimensioned to pass through a selected portion of an anatomy such as a bore or tunnel formed in a femur. It will be understood, however, that the dimension of the cross member 426, either alone or in combination with the main body portion 424, can be used to engage a side or surface of the anatomy to anchor the anchor member 422 relative to a portion of the anatomy.

Figure 20:
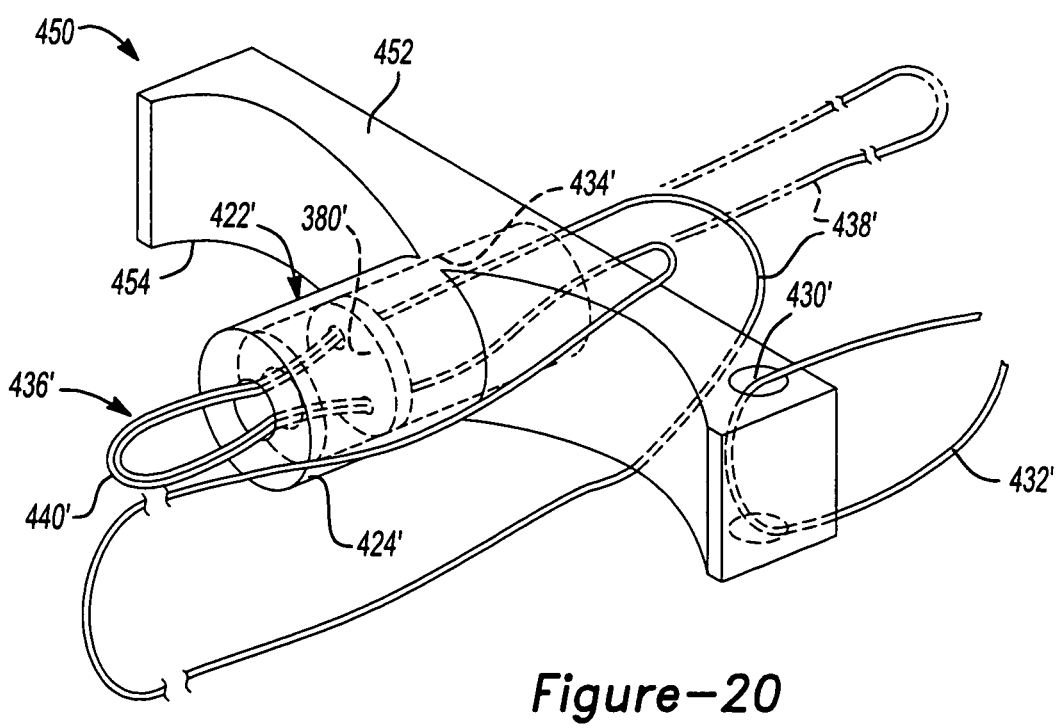
FIG. 20 is a perspective view of an anchor assembly according to various embodiments.

With reference to FIG. 20, an anchor assembly 450 is illustrated. The anchor assembly 450 can be similar to the anchor assembly 420 and similar portions are referenced with similar numerals augmented with a prime and not again discussed in detail. The anchor assembly 450 includes a main body 424 similar to the main body 424 of the anchor assembly 450. Nevertheless, the anchor assembly 450 also includes a cross member 452 that extends a distance from the main body 454 to define an edge or surface 454.

The edge 454 can define an arc or a radius such that the edge 454 is curved. The upper surface of the cross member 452 may also be radiused according to various embodiments. The radiused edge 454 can be provided for various reasons, such as increased purchase on a bone, matching a curvature of a bone, or various other reasons. According to various embodiments, the cross member 452 can engage a selected portion of the anatomy to assist in holding the anchor assembly 450 in a selected position.

The anchor assembly 450, and anchor assemblies according to various embodiments, can include a collar portion 380' similar to the collar portion 380 illustrated in the anchor assembly 350'. Therefore, the flexible member 436 can be used in conjunction with the collar member 380 that is positioned within the bore 454' to assist in moving the flexible member 436 relative to a selected portion of the anatomy and to engage a soft tissue or graft member. The flexible 436' can also include the graft engagement portion 440' and an actuation end 438' similar to those discussed above.

With reference to FIG. 21, an exemplary method of using the anchor assembly 420 as illustrated. It will be understood that the exemplary method of the use of the anchor 420 can be used with any various embodiments, such as any of the other appropriate anchor members described above including the anchor member 450. Further, the method of use is merely exemplary for the anchor member 420 and the method of using the anchor member 420 can be similar to the method described in FIG. 16-18 or according to various other embodiments.

For example, the tibia 396 and the femur 270 can be prepared with tunnels 394, 272, respectively, in preparation for moving the anchor assembly 420 therethrough and positioning the soft tissue graft 274 relative thereto. It will also be understood that the tibia 396 and the femur 270 can be prepared according to any appropriate method such as those generally known in the art. Therefore, the specifics of preparing the femur 270 and the tibia 396 are not described in detail.

Once the tunnels 394, 272 are formed in the tibia 396 and femur 270, the movement member 432 can be passed through the tunnels 394, 272 according to any appropriate method. The movement member 432 can then be moved in the direction of arrow 460 to draw the anchor assembly 420 through the tunnels 394, 272 formed in the tibia 396 and femur 270. The graft engagement portion 440 of the flexible member can be interconnected with the soft tissue graft 274, as illustrated in FIG. 22, or can be held relative to the tibia 396 as the graft assembly 420 is passed through the tunnels 394, 272.

The activating portion 438 of the flexible strand 436 can be interconnected with the anchor body 422 in any appropriate manner. For example, a portion of the activation portion 438 of the flexible member 436 can be looped over one of the portions of the cross member 426. In this way, the activation portion 438 of the flexible strand 436 can be held relative to the anchor assembly 420 in a manner operable to allow ease of use or access once the anchor body 422 is passed through the tunnels 272, 394.

It will be understood that the actuation member 438, according to various embodiments, can also be moved in any appropriate manner to allow for activation of the graft engaging portion 440. For example, the activation portion or end 438 can be passed through the tunnels 394, 272, as illustrated in phantom 438a with the guiding flexible member 432. The activation end 438a can then be positioned relative to the guide portion 432 to be used to activate the graft engaging portion 440 at any appropriate time. It will also be understood that the guiding flexible member 432 can be moved through the tunnels 394, 272 in any appropriate manner and the activation end 438a can be moved therewith. The activation member 438 can also be provided to extend from the graft anchor member 420 to extend exterior to the anatomy as the anchor member 420 passes through the tunnels 394, 272, as illustrated in FIG. 22. Thus, the activation member 438b, shown in phantom, can be activated from a selected side of the anatomy as the anchor is positioned relative to the femur 270. It will also be understood that the anchor 422 need not be passed to an exterior of the soft tissue of the member, such as the joint. As such, the anchor may be passed just exterior to the bone 270, such as just passed an end of the tunnel 272 and thereby activated to engage the bone 270. The anchor 422 also does not need to pass exterior to the soft tissue or any tissue surrounding the bone 270. Thus, the positioning of the activation members 438a, 438b can be done to facilitate a positioning of the anchor 422. The activation portion 438 can be positioned around the anchor 422 and moved with the anchor 422 through the tunnels 394, 272 if it is selected to move the anchor 422 to a position for grasping or engaging the activation member 438.

With continuing reference to FIG. 22, as the anchor body 422 is passed through the tunnels 394, 272, the anchor body 422 can assume an orientation that allows for ease of moving of the anchor body 422 through the tunnel 394, 272. Therefore, the anchor body 422 can move through the tunnels 394, 272 to allow for movement of the graft 274 relative to the tunnels 394, 272. Further, as illustrated in FIG. 22, once the anchor body 422 has passed out of the tunnel 272 formed in the femur 270, the anchor body 422 can be oriented to allow for at least a portion thereof, such as the cross member 426, to engage a portion of the femur 270. For example, the edge 428 can engage the femur 270 to resist movement of the anchor body 422 back into the tunnel 272. The movement member 432 can be used to manipulate the anchor body 422 through the tunnel 394, 272 and to orient the anchor body 422 relative to the femur 270.

The activation portion 438 of the flexible member can then be moved generally in the direction of arrow 470 to draw the graft engaging portion 440 of the flexible member generally in the direction of arrow 472 through the tunnels 394, 272. As the activation member portion 438 of the flexible member 436 is pulled, the graft engaging portion 440 pulls the graft 274 through the tunnels, as discussed above. It will be understood that the activation portion 438 can be manipulated prior to setting the anchor body 422 and the tunnel 272 or after the anchor member 422 has been set into the tunnel 272. Regardless, the movement of the activation member 428 can be possible due to various reasons, including those discussed above.

Figure 23:
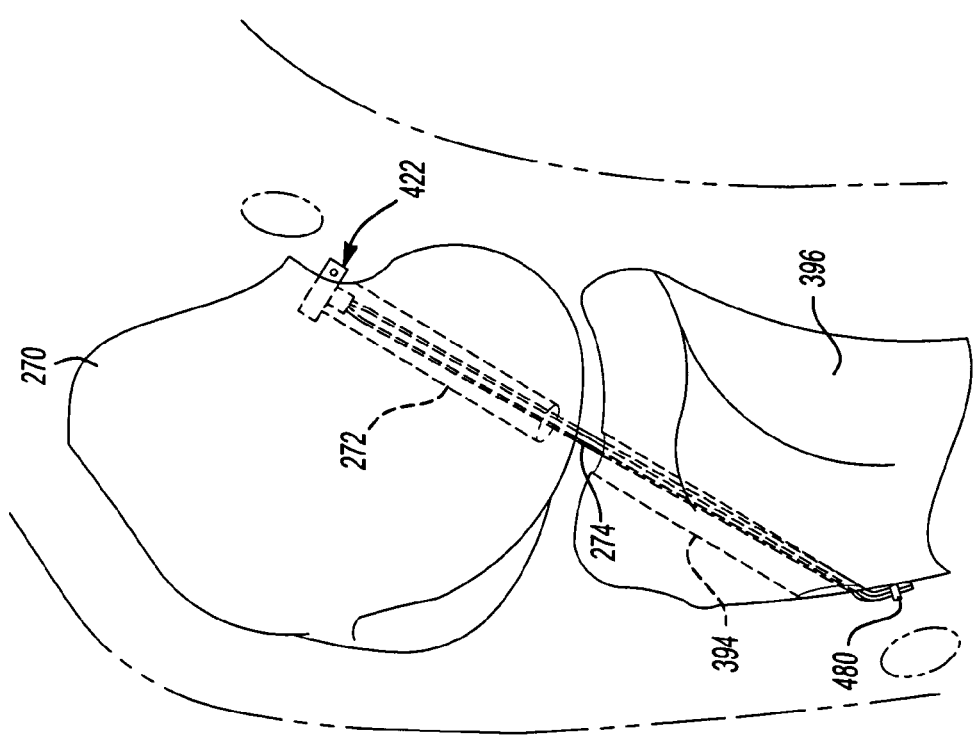

Turning reference to FIG. 23, once the graft 274 has been positioned in the tunnels 394, 272, the anchored member 422 can be set relative to the femur 270, at least in part, by tensioning the soft tissue member 274 relative to the femur 270 and the tibia 396. As discussed above, various methods and techniques can be used for tensioning the graft 274 relative to the femur 270 and the tibia 396. Further, a fixation member 480 can be used to fix the graft 274 relative to the tibia 396. As discussed above, the fixation member 480 can be any appropriate fixation member, such as the WasherLoc® provided by Arthrotek, Inc. of Warsaw, Ind. Nevertheless, the tensioning of the graft 274 can assist in setting the anchor 422 into and relative to the femur 270. One will understand, however, that any appropriate method can be used to set the anchor body 422 relative to the femur 270 and assist in assuring that the anchor body 422 does not pass back through the tunnel 272.

In light of the foregoing, one skilled in the art will understand that an anchor assembly can be used according to various methods to position the graft 274 relative to various portions of the anatomy, such as the tibia 396 and the femur 270. It will be understood that the anchor assemblies according to various embodiments can be used to interconnect, with a graft of any appropriate type, any appropriate bone portions. Further, it will be understood that the graft 274 can be synthetic or natural and can formed from an allograft, an autograft, or a xenograft or combinations thereof. Further, it will be understood that various features according to various embodiments can be used together to achieve a selected result. For example, the moveable loop 374 or 440 according to various embodiments can be used with various members other than those with which they are specifically illustrated. One skilled in the art will understand that various features can be combined to achieve selected results and achieve a selected result.

Nevertheless, the anchor bodies according to various embodiments can be used to anchor a graft relative to a selected portion of an anatomy for fixation of the graft relative to the portion of the anatomy. The anchor assembly can be manipulated by a user through various openings, such as small openings in the anatomy to achieve a less invasive procedure. Further, the anchor assemblies can be used to assist in providing a result in various procedures, such as open, arthroscopic, or the like.

The teachings are merely exemplary in nature and, thus, variations that do not depart from the gist of the teachings are intended to be within the scope of the teachings. Such variations are not to be regarded as a departure from the spirit and scope of the teachings.

What is claimed is:

1. An anchor assembly for anchoring a graft to an anatomy, comprising:
   an anchor body member having a cross-member and a main body operable to be positioned in the anatomy, the anchor body member defining a through bore having first and second generally cylindrical sections, the through bore first section having a first interior cross-sectional area, and the second section having a second interior cross-sectional area greater than the first interior cross-sectional area;
   a collar wholly disposed within the second section, said collar defining a first collar through bore and a second collar through bore that extends substantially parallel to the first collar through bore;
   a surface extending from the anchor body operable to engage the anatomy and to resist movement of the anchor body into the anatomy;
   a selectable graft engagement member disposed through the collar through bore; and
   an activation member operably connected with the selectable graft engagement member to select a size of the graft engagement member.

2. The anchor assembly of claim 1, wherein at least one of the selectable graft engagement member, the activation member, or combinations thereof are a flexible member.

3. The anchor assembly of claim 2, wherein the graft engagement member and the activation member are both flexible members.

4. The anchor assembly of claim 3, wherein the graft engagement member and the activation member are a same flexible member.

5. The anchor assembly of claim 3, wherein the graft engaging member and the activation member are interconnected through a passage defined in the anchor body member.

6. The anchor assembly of claim 1, wherein the collar is disk-shaped.

7. The anchor assembly of claim 6, wherein said cross member is substantially straight, curved, polygonal, or combinations thereof.

8. The anchor assembly of claim 1, wherein the activation member is interconnected with the graft engagement member through a selectable engagement system.

9. The anchor assembly according to claim 1, wherein the cross member defines a pair of concave anatomy engagement surfaces.

10. The anchor assembly according to claim 1, wherein the collar defines a pair of flexible graft engagement members.

11. An anchor assembly to anchor a graft in an anatomy comprising:
    an anchor body having a cross-member and a cylindrical portion, the anchor body defining a generally cylindrical passage through the cross-member and cylindrical portion, the passage having an internal shoulder defined in the cylindrical portion; and
    a collar disposed within the passage, said collar defining a first collar through bore and a second collar through bore, each of which have a diameter less than a diameter of the passage in the cross-member;
    a flexible member extending through the passage defined by the anchor body and through both the first collar through bore and the second collar through bore;
    wherein the flexible member defines a graft engaging portion and a selection portion, the graft engaging portion includes a graft engaging loop with a first end extending from the first collar through bore and a second end extending from the second collar through bore;
    wherein the selection portion extends a distance to be moved by a user to select a size of the graft engaging portion.

12. The anchor assembly of claim 11, further comprising:
    a cross member operable to engage the anatomy to resist movement of the anchor body into the anatomy.

13. The anchor assembly of claim 11, wherein the selection portion includes a selection loop having a first end extending from the first collar through bore and a second end extending from the second collar through bore; and
    wherein the graft engaging loop is integral with the selection loop such that the flexible member defines a single continuous loop.

14. The anchor assembly of claim 11, further comprising:
    a selection system operably interconnected with the flexible member to allow the selection portion to select a size of the graft engaging portion.

15. The anchor assembly of claim 11, wherein the anchor body includes a dimension operable to move through a bore formed in the anatomy.

16. The anchor assembly of claim 11, further comprising:
    an orientation selection mechanism operable to move the anchor body from a first orientation to a second orientation relative to the anatomy.

17. The anchor assembly of claim 16, wherein the anchor body is operable to move through a bore formed in the anatomy in a first orientation and move to a second orientation when positioned exterior to the bore;
    wherein a holding member is operable to engage the anatomy in the second orientation to hold the anchor body in a selected orientation relative to the anatomy.

18. The anchor assembly according to claim 11, wherein the passage has first and second sections, said first section having a first cross-sectional area, and said second section has a second section having a second cross-sectional area larger than the first cross-sectional area, and wherein the collar is disposed in the second section.

19. An anchor assembly for anchoring a graft to an anatomy, said anchor assembly comprising:
    an anchor body having a cross-member with a bone engaging surface, said anchor body further having a generally cylindrical body, said cylindrical body defining a body through bore, said through bore having a first generally cylindrical portion having a first internal cross-sectional area and a second generally cylindrical portion having a second internal cross-sectional area greater than the first internal cross-sectional area;

a collar wholly disposed within the second section, said collar defining a first collar through bore;

a flexible graft engagement member, said selectable graft engagement member being disposed through the body through bore and the first collar through bore;

a guide bore defined by the cross-member, the guide bore extends transverse to the body through bore; and a guiding member extending through the guide bore.

20. The anchor assembly according to claim 19, wherein the collar defines a second collar through bore, and wherein the selectable flexible graft engagement member is disposed through the second collar through bore.

21. The anchor assembly according to claim 19, wherein the body comprises a cross member defining a pair of concave engagement surfaces configured to engage the anatomy.

22. The anchor assembly according to claim 19, further comprising an activation member connected to the selectable flexible graft engagement member to select the size of the selectable flexible graft engagement member.

* * * * *

UNITED STATES PATENT AND TRADEMARK OFFICE
CERTIFICATE OF CORRECTION

PATENT NO. : 8,109,965 B2
APPLICATION NO. : 11/541504
DATED : February 7, 2012
INVENTOR(S) : Kevin T. Stone et al.

It is certified that error appears in the above-identified patent and that said Letters Patent is hereby corrected as shown below:

On the Title Page, Item [73], Assignee, "Biomet Sports Medicine, LLP" should be --Biomet Sports Medicine, LLC--.

On the Title Page, Item [56], References Cited, U.S. Patent Documents, Column 2, reference 2, "828,203  12/1906  Neil" should be --838,203  12/1906  Neil--.

On the Title Page, Item [56], References Cited, U.S. Patent Documents, the following reference is not shown on patent, insert --6,062,344  11/1991  Gerker--.

In the Specifications:
Column 1, line 51, after "insure" delete "that".
Column 1, line 61, "anatomicat" should be --anatomical--.
Column 2, line 58, "movement a the anchor" should be --movement of the anchor--.
Column 2, line 59, after "member" delete "and".
Column 3, line 8, "and" should be --as--.
Column 3, line 57, "an cross-sectional" should be --a cross-sectional--.
Column 3, line 62, "an partially" should be --a partially--.
Column 5, line 58, "a activation" should be --an activation--.
Column 5, line 59, "a activation" should be --an activation--.
Column 6, line 11, "a activation" should be --an activation--.
Column 6, line 12, "a activation" should be --an activation--.
Column 6, line 37, "a activation" should be --an activation--.
Column 6, line 42, "a activation" should be --an activation--.
Column 8, line 53, "a activation" should be --an activation--.
Column 8, line 56, "a activation" should be --an activation--.
Column 9, line 25, "a activation" should be --an activation--.
Column 9, line 59, "a activation" should be --an activation--.

Signed and Sealed this
Seventeenth Day of September, 2013

Teresa Stanek Rea
*Deputy Director of the United States Patent and Trademark Office*

CERTIFICATE OF CORRECTION (continued)
U.S. Pat. No. 8,109,965 B2

In the Specification:

Column 11, line 31, after "formed" insert --of--.
Column 13, line 6, "a end" should be --an end--.
Column 14, line 39, "the a portion" should be --the portion--.
Column 15, line 3, "nitinol" should be --Nitinol--.
Column 15, line 58, after "relative" insert --to--.
Column 18, line 13, "not" should be --knot--.
Column 18, line 55, "though" should be --through--.
Column 21, line 8, after "flexible" insert --member--.
Column 21, line 12, "as" should be --is--.
Column 21, line 19, "FIG. 16-18" should be --FIGS. 16-18--.
Column 22, line 66, after "can" insert --be--.
Column 23, lines 7-8, after "selected results" delete "and achieve a selected result".